(12) United States Patent
Hide et al.

(10) Patent No.: US 9,989,538 B2
(45) Date of Patent: Jun. 5, 2018

(54) MONOCLONAL IGE ANTIBODY THAT BINDS TO SWEAT ALLERGY ANTIGEN PROTEIN

(71) Applicant: Hiroshima University, Higashihiroshima-shi, Hiroshima (JP)

(72) Inventors: Michihiro Hide, Hiroshima (JP); Kaori Ishii, Hiroshima (JP); Makiko Hiragun, Hiroshima (JP)

(73) Assignee: Hiroshima University, Hiroshima (JP)

( * ) Notice: Subject to any disclaimer, the term of this patent is extended or adjusted under 35 U.S.C. 154(b) by 232 days.

(21) Appl. No.: 14/421,821

(22) PCT Filed: Aug. 9, 2013

(86) PCT No.: PCT/JP2013/071715
§ 371 (c)(1),
(2) Date: Feb. 14, 2015

(87) PCT Pub. No.: WO2014/027626
PCT Pub. Date: Feb. 20, 2014

(65) Prior Publication Data
US 2015/0212097 A1 Jul. 30, 2015

(30) Foreign Application Priority Data
Aug. 17, 2012 (JP) ................ 2012-181051

(51) Int. Cl.
| | |
|---|---|
| G01N 33/53 | (2006.01) |
| G01N 33/68 | (2006.01) |
| C07K 16/14 | (2006.01) |
| C07K 16/40 | (2006.01) |
| C07K 16/18 | (2006.01) |

(52) U.S. Cl.
CPC ......... *G01N 33/6893* (2013.01); *C07K 16/14* (2013.01); *C07K 16/18* (2013.01); *C07K 16/40* (2013.01); *G01N 33/6854* (2013.01); *C07K 2317/21* (2013.01); *C07K 2317/76* (2013.01); *G01N 2333/37* (2013.01); *G01N 2800/202* (2013.01); *G01N 2800/24* (2013.01)

(58) Field of Classification Search
CPC ........ C07K 16/14; C07K 16/18; C07K 16/40; C07K 2317/21; C07K 2317/76; G01N 2333/37; G01N 2800/202; G01N 2800/24; G01N 2800/20; G01N 22/6893; G01N 33/6854; G01N 33/53
See application file for complete search history.

(56) References Cited

U.S. PATENT DOCUMENTS

| | | |
|---|---|---|
| 2006/0088926 A1 | 4/2006 | Ozawa et al. |
| 2006/0134706 A1 | 6/2006 | Hide et al. |
| 2010/0311604 A1 | 12/2010 | Takkinen et al. |
| 2011/0117103 A1 | 5/2011 | Hide et al. |
| 2015/0238581 A1 | 8/2015 | Hide et al. |

FOREIGN PATENT DOCUMENTS

| | | |
|---|---|---|
| EP | 0955366 A1 | 11/1999 |
| EP | 1607107 A1 | 12/2005 |
| EP | 1655307 A1 | 5/2006 |
| EP | 2292659 A1 | 3/2011 |
| JP | 3642340 B2 | 4/2005 |
| JP | 2008-069118 A | 3/2008 |
| JP | 2010-516747 A | 5/2010 |
| WO | 2003/084991 A1 | 10/2003 |
| WO | 2005/005474 A1 | 1/2005 |
| WO | 2008/092993 A1 | 8/2008 |
| WO | 2009/133951 A1 | 11/2009 |

OTHER PUBLICATIONS

Lazar et al., (Mol Cell Biol 8(3):1247-52 (1988).*
Rudikoff et al. (PNAS USA, 1982, 79: 1979-1983).*
Coleman et al. (Research in Immunology, 1994; 145(1): 33-36).*
Skolnick et al. (TIBTECH 18:34-39, 2000).*
International Search Report issued in corresponding International Patent Application No. PCT/JP2013/071715 dated Nov. 12, 2013.
Human IgE (Non-Immune), 2011, BIOPORTO Diagnostics.
Shindo et al., "Histamine release-neutralization assay for sera of patients with atopic dermatitis and/or cholinergic urticaria is useful to screen type I hypersensitivity against sweat antigens," Archives of Dermatological Research, 304: 647-654 (2012).
Xu et al., "hypothetical protein MGL_1304 [Malassezia globosa CBS 7966]," RefSeq. [online], XP_001732036.1 (2008).
Hiragun et al., "Fungal protein MGL_1304 in sweat is an allergen for atopic dermatitis patients," Journal of Allergy and Clinical Immunology, 132: 608-615 (2013).
Steinberger et al., "Construction of a Combinatorial IgE Library from an Allergic Patient," The Journal of Biological Chemistry, 271: 10967-10972 (1996).
Tanaka et al. "Cholinergic Urticaria Successfully Treated by Immunotherapy with Partially Purified Sweat Antigen," Allergy, 56: 54-57 (2007) (see English abstract).
Tanaka et al., "Semi-purification of the immunoglobulin E-sweat antigen acting on mast cells and basophils in atopic dermatitits," Experimental Dermatology, 15: 283-290 (2006).
Fairley et al., "A Pathogenic Role for IgE in Autoimmunity: Bullous Pemphigoid IgE Reproduces the Early Phase of Lesion Development in Human Skin Grafted to nu/nu Mice," Journal of Investigative Dermatology, 127: 2605-2611 (2007).
International Preliminary Report on Patentability and Written Opinion issued in corresponding International Patent Application No. PCT/JP2013/071715 dated Feb. 26, 2015.
International Search Report issued in related International Patent Application No. PCT/JP2013/067396 dated Jul. 23, 2013.
International Preliminary Report on Patentability issued in related International Patent Application No. PCT/JP2013/067396 dated Dec. 28, 2014.
Xu et al., "Malassezia globosa CBS 7966 hypothetical protein MGL_1304 partial mRNA," Database DDBJ/EMBL/GenBank Accession No. XM_001731984.1 (2008).

(Continued)

*Primary Examiner* — Tracy Vivlemore
*Assistant Examiner* — Carmencita M Belei
(74) *Attorney, Agent, or Firm* — Morgan, Lewis & Bockius LLP

(57) ABSTRACT

Provided include a human IgE antibody that binds to a sweat allergy antigen protein and a human high-affinity IgE receptor but does not induce degranulation in a reaction with the sweat allergy antigen protein, and a composition for treatment or diagnosis of sweat allergy comprising the same.

4 Claims, 12 Drawing Sheets

(56) References Cited

OTHER PUBLICATIONS

Rasool et al., "Cloning, characterization and expression of complete coding sequences of three IgE binding Malassezia furfur allergens, Mal F 7, Mal f 8 and Mal f 9," European Journal of Biochemistry, 267: 4355-4361 (2000).
Lindborg et al., "Malassezia furfur mRNA coding for potential allergen, strain ATCC No. 42132," Database DDBJ/EMBL/GenBank Accession No. AJ011958.1 (2000).
Lindborg et al., "Malassezia sympodialis mRNA for allergen Mal s 8, strain ATCC No. 42132," Database DDBJ/EMBL/GenBank Accession No. AJ011958.2 (2002).
Kanbe et al., "Atopic *dermatitis* and *malassezia* Species: A Study of Antigenic Components of *malassezia* Species for Immunoglobulin E of Patients with Atopic Dermatitits," Japanese Journal of Medical Mycology, 44: 71-75 (2003) (see English abstract).
Extended European Search Report issued in corresponding European Patent Application No. 13809354.7 dated Feb. 10, 2016.
Valenta et al., "Autoallergy: A pathogenetic factor in atopic dermatitis?" Journal of Allergy and Clinical Immunology, 105: 432-437 (2000).
Vilhelmsson, "Structural and functional studies of malassezia sympodialis-derived allergens," Department of Medicine Solna, Clinical Allergy Research Unit, Karolinska Institutet, XP55234699 (2008).
Partial Supplementary European Search Report issued in related European Patent Application No. 13879589.3 dated Apr. 20, 2016.
Ishii et al., "A human monoclonal IgE antibody that binds to MGL_1304, a major allergen in human sweat, without activation of mast cells and basophils," Biochemical and Biophysical Research Communications, 468: 99-104 (2015).
"Product Catalog 2010 Bioporto Diagnostics," XP055257898, http://www.ngal.cz/files/bioporto-katalog-2010-en.pdf (2010).

\* cited by examiner

Distribution of QRX amount on body surface

MONOCLONAL IGE ANTIBODY THAT BINDS TO SWEAT ALLERGY ANTIGEN PROTEIN

A computer readable text file, entitled "SequenceListing.txt," created on or about Feb. 12, 2015 with a file size of about 7 kb contains the sequence listing for this application and is hereby incorporated by reference in its entirety.

TECHNICAL FIELD

This application claims priority to Japanese Patent Application No. 2012-181051, filed Aug. 17, 2012 and incorporated by reference herein in its entirety.

The present invention primarily relates to a human IgE antibody that binds to a sweat allergy antigen, a method of screening or manufacturing the human IgE antibody, use of the human IgE antibody in detection or measurement of a sweat allergy antigen contained in human sweat, use of the human IgE antibody in detection or measurement of an antibody that binds to a sweat allergy antigen contained in human sweat, and use of the human IgE antibody in neutralization or removal of a sweat allergy antigen.

BACKGROUND

An allergy reaction is referred to as an immediate-type or a type-I hypersensitive reaction and is mediated by an IgE antibody. When a living body is exposed to an allergen for the first time, an IgE-antibody-producing B cell starts producing a soluble IgE molecule. The soluble IgE molecule binds to a high-affinity IgE receptor present on a surface of mast cells or a basophils. If the living body encounters the same allergen again, the high-affinity IgE receptor is cross-linked with the IgE antibody by the allergen, causing the allergy reaction in which histamine and cytokine are released from a cell.

Anti-IgE antibodies that neutralize IgE antibodies are put into practical use as antibodies for suppressing the allergy reaction. However, a human IgE antibody that binds to the high-affinity IgE receptor has a property of activating mast cells and basophils solely or in combination with the allergen further binding thereto. Therefore, in general, the human IgE antibody is not considered to be useful for neutralization of the allergen.

On the other hand, manufacturing of a human antibody is no longer a difficult technique and a human antibody can be prepared with various methods (e.g., an Epstein-Barr virus (EBV) immortalization method, a phage display method, and a complete human antibody producing hybridoma method).

Human IgE monoclonal antibodies are also reported as being manufactured by using a phage display method, for example (Patent Document 1, Non-Patent Literature 1).

CITATION LIST

Patent Document

Patent Document 1: Japanese Unexamined Patent Application Publication (Translation of PCT Application) No. 2010-516747

Non-Patent Literature

Non-Patent Literature 1: Steinberger P. et al., (1996) J. Biol. Chem. 271, 10967-10972

SUMMARY OF THE INVENTION

The present inventors purified a human sweat antigen from human sweat based on the histamine release activity from peripheral blood basophils of atopic dermatitis patients and identified by mass spectrometry that the human sweat antigen was MGL_1304, which is a protein derived from *Malassezia globosa*. The present inventers also identified a human IgE antibody that specifically binds to a human sweat antigen.

In one aspect, the present invention provides a human IgE antibody or an antibody fragment thereof that binds to a sweat allergy antigen protein and a human high-affinity IgE receptor but does not induce degranulation in a reaction with the sweat allergy antigen protein, a method of screening the antibody, and a method of manufacturing the antibody.

In one aspect, the present invention provides a composition for treatment of sweat allergy or a disease related to a sweat allergy antigen, a composition for removal or neutralization of a sweat allergy antigen, or a material for removal of a sweat allergy antigen, comprising a human IgE antibody or an antibody fragment thereof that binds to a sweat allergy antigen protein and a human high-affinity IgE receptor but does not induce degranulation in a reaction with the sweat allergy antigen protein.

In one aspect, the present invention provides a composition or kit for detection of a human sweat allergy antigen protein, or for measurement of the amount of a human sweat allergy antigen protein, comprising a human IgE antibody or an antibody fragment thereof that binds to a sweat allergy antigen protein and a human high-affinity IgE receptor but does not induce degranulation in a reaction with the sweat allergy antigen protein.

In one aspect, the present invention provides a composition or kit for detection of an antibody that binds to a human sweat allergy antigen protein, or for measurement of the amount of an antibody that binds to a human sweat allergy antigen protein, which comprises a standard substance, wherein the standard substance is a human IgE antibody that binds to a sweat allergy antigen protein and a human high-affinity IgE receptor but does not induce degranulation in a reaction with the sweat allergy antigen protein.

BRIEF DESCRIPTION OF DRAWINGS

A recombinant protein of MGL_1304 was produced by *E. coli*.

In FIG. 4, B shows correlation of the histamine release activity between a partially purified sweat antigen (QR) and MGL_1304 recombinant protein (rMGL_1304).

M: molecular weight marker;
QRX: partially purified sweat antigen;
rMGL (Full): recombinant MGL_1304 full-length protein;
Lys: extract obtained by ultrasonic fragmentation of a fungus body of *Malassezia globosa* and PBS (−) extraction followed by removal of residues through a 0.22-μm filter;
dsp: polypeptide corresponding to the amino acid sequence 22 to 183 of the recombinant MGL_1304 protein that is obtained by removing a signal peptide from the recombinant MGL_1304 protein;
Full: recombinant MGL_1304 full-length protein;
P2-4: polypeptide corresponding to the amino acid sequence 46-183 of the MGL_1304 protein;
P1: polypeptide corresponding to the amino acid sequence 1-50 of the MGL_1304 protein;
P2: polypeptide corresponding to the amino acid sequence 46-100 of the MGL_1304 protein;
P3: polypeptide corresponding to the amino acid sequence 96-140 of the MGL_1304 protein; and
P4: polypeptide corresponding to the amino acid sequence 136-183 of the MGL_1304 protein.

Figure 18:
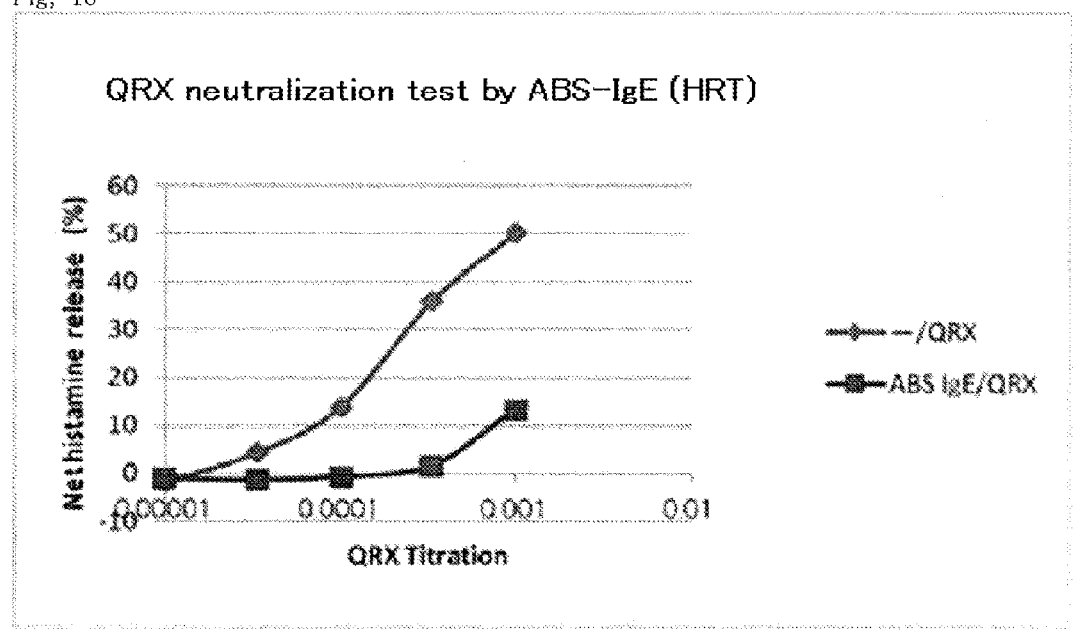

FIG. 18 shows that the ABS IgE antibody suppresses histamine release induced by adding QRX to basophils derived from a sweat allergy patient. In FIG. 18, −/QRX represents the histamine release when QRX is added to basophils derived from a sweat allergy patient, and ABS IgE/QRX represents the histamine release when QRX and the ABS IgE antibody are added to basophils derived from the sweat allergy patient.

Figure 19:
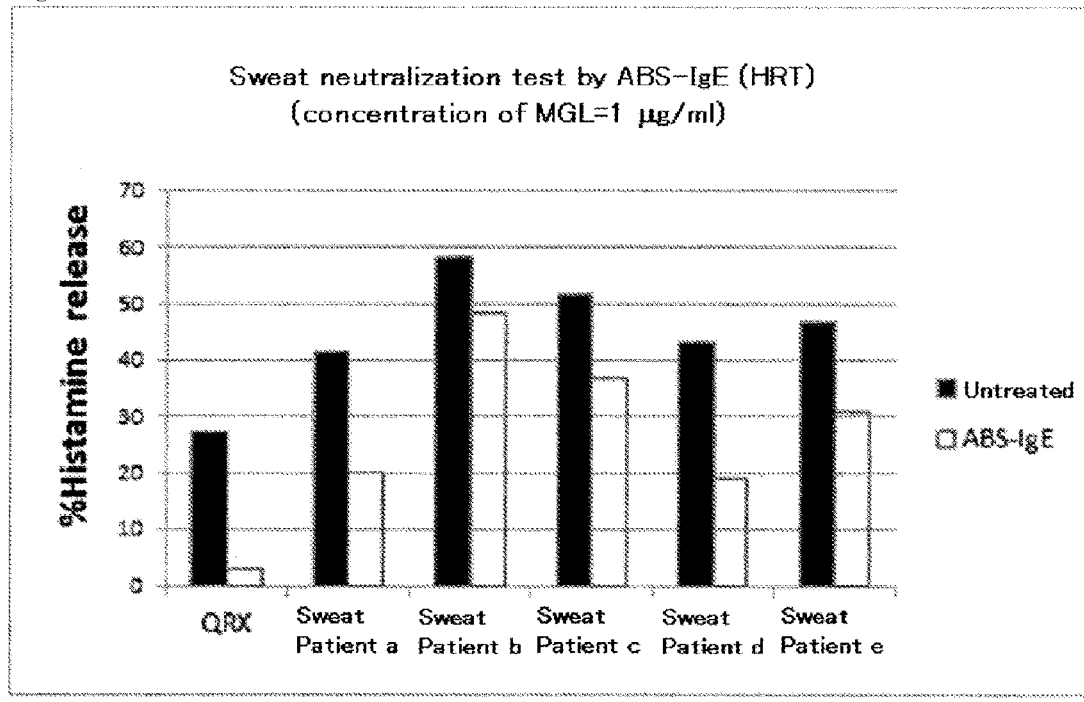

FIG. 19 shows that the ABS IgE antibody suppresses histamine release from basophils derived from sweat allergy patients induced by unpurified human sweat. In FIG. 19, "untreated" represents the histamine release activity when the ABS IgE antibody is not added to basophils derived from sweat allergy patients, and "ABS-IgE" represents the histamine release activity when the ABS IgE antibody (1 μg/ml) is added to basophils derived from the sweat allergy patients.

Figure 20:
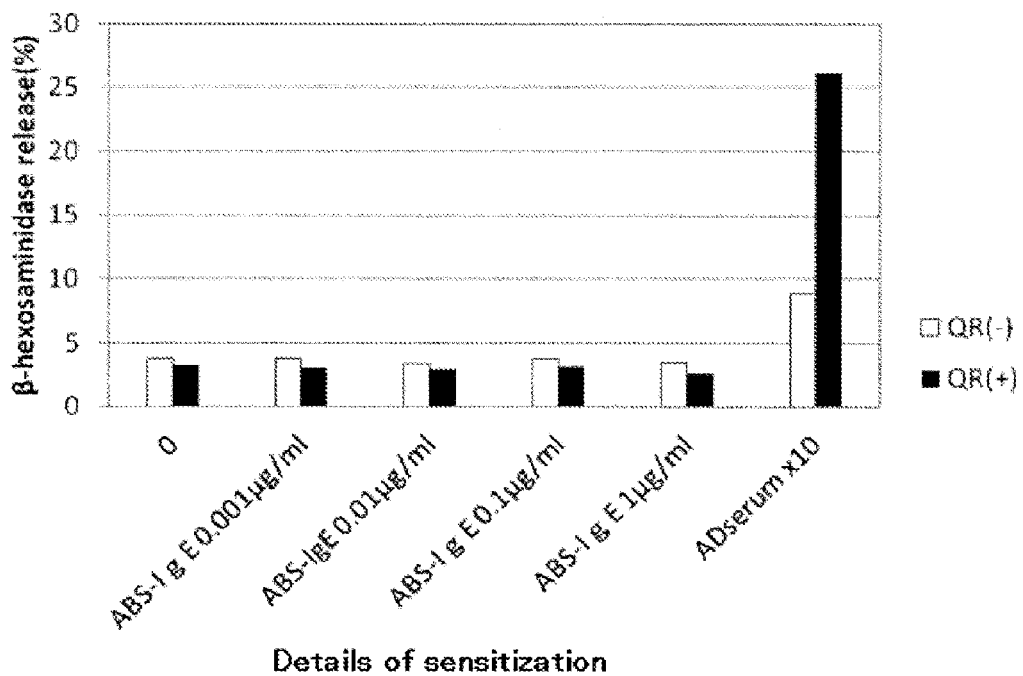

FIG. 20 shows that degranulation is not induced by stimulation with QRX in rat mast cells expressing a human high-affinity IgE receptor which have been sensitized by the ABS IgE antibody. In FIG. 20, the right column (black) indicates β-hexosaminidase release % at the time of stimulation by 200-fold diluted QRX, and the left column (white) indicates β-hexosaminidase release % without stimulation.

Figure 21:
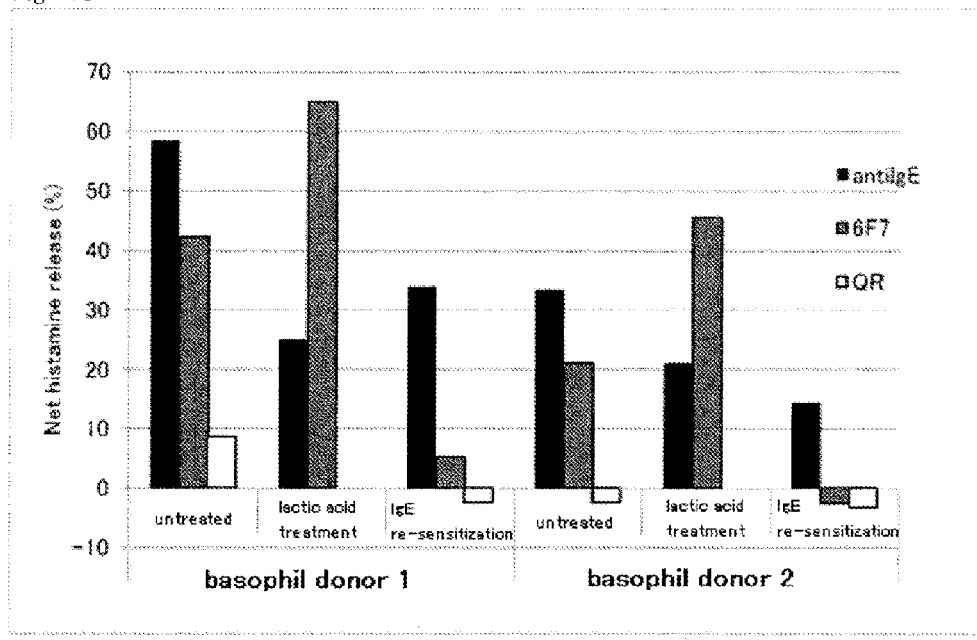

FIG. 21 shows that degranulation was not observed when basophils prepared from two blood samples derived from different persons were sensitized by the ABS IgE antibody and stimulated by QRX. The left column indicates the histamine release percentage (net %) at the time of stimulation by an anti-human IgE antibody (anti-IgE), the middle column indicates the histamine release at the time of stimulation by 6F7 that is an IgE-competitive anti-IgE receptor monoclonal antibody, and the right column indicates the histamine release percentage at the time of stimulation by QRX.

Figure 22:
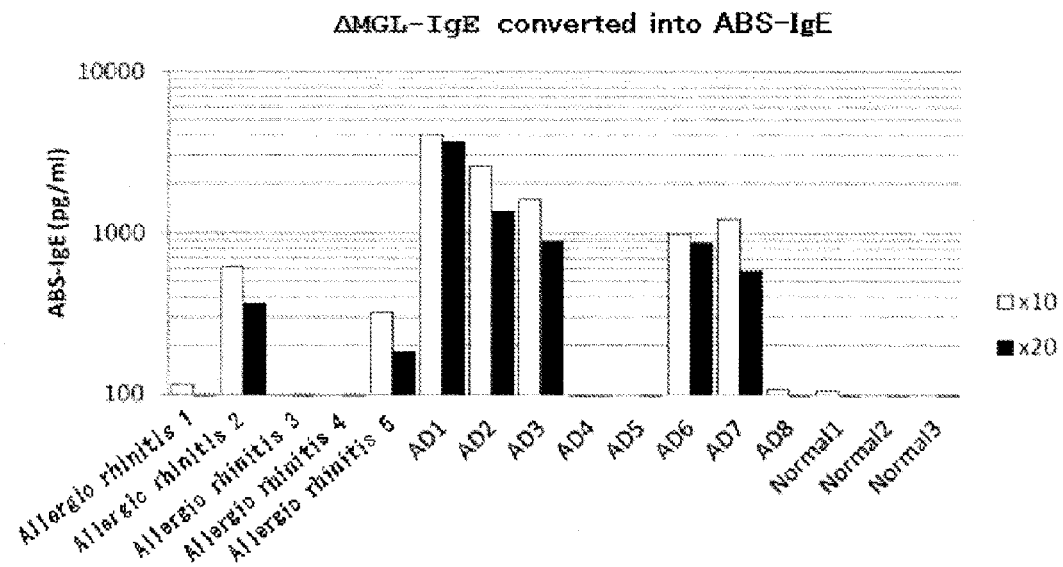

FIG. 22 shows the result of quantification of IgE antibody that specifically binds to the MGL_1304 recombinant protein (rMGL) in serums of allergic rhinitis patients (allergic rhinitis 1-5), atopic dermatitis patients (AD1-8), and healthy persons (Normal-3). For quantification, an ELISA plate was coated with rMGL, and the amount of IgE antibody that specifically bound to rMGL in the serums was measured. The serum was diluted 10 times (×10) or 20 times (×20) prior to the test. The amount of bound IgE was measured by using an HRP-anti-human IgE antibody based on the absorbance at 450 nm. The absorbance was then converted into pg/ml by using the standard curve shown in FIG. 9 that was obtained by using the ABS IgE antibody as a standard substance.

Figure 23:
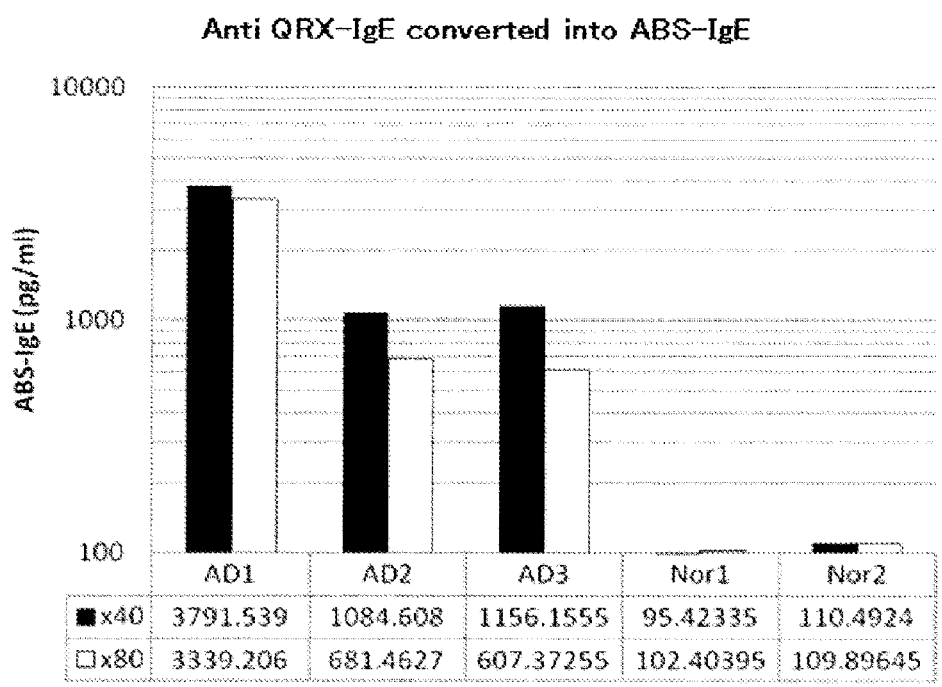

FIG. 23 shows the result of quantification of IgE antibody that specifically binds to the partially purified sweat antigen protein (QRX) in serums of atopic dermatitis patients (AD1-3) and healthy persons (Nor1-2). For quantification, the Smith2 antibody was immobilized on an ELISA plate and bound to QRX to measure the amount of IgE antibody bound to the ORX in the serums. The serum was diluted 40 times (×40) or 80 times (×80) prior to the test. The amount of bound IgE was measured by using an HRP-anti-human IgE antibody based on the absorbance at 450 nm. The absorbance was then converted into pg/ml by using the standard curve shown in FIG. 16 that was obtained by using the ABS IgE antibody as a standard substance.

MODES FOR CARRYING OUT THE INVENTION

1. Human IgE Antibody or Antibody Fragment that Binds to Sweat Allergy Antigen Protein and Human High-Affinity IgE Receptor but Does Not Induce Degranulation with Sweat Allergy Antigen Protein, and Method of Manufacturing the Same In a first aspect, the present invention provides a human IgE antibody or an antibody fragment that binds to a sweat allergy antigen protein and a human high-affinity IgE receptor but does not induce degranulation in a reaction with the sweat allergy antigen protein, and a method of manufacturing the same.

As used herein, a sweat allergy antigen protein is a protein that is an antigen of sweat allergy, and may be a protein that is a partially purified protein obtained from human sweat by a known method (e.g., Toshihiko Tanaka, et al., Allergy 56: 54-57, 2007; Tanaka A, et al. Exp Dermatol 15: 283-290, 2006, and WO 2009-133951), or a protein produced by a microorganism: *Malassezia globosa* (e.g., *Malassezia globosa* (No. MYA-4612) purchasable from ATCC), and binds to serum derived from a sweat allergy patient and/or Smith2 antibody (Accession No. FERM BP-11111). The sweat allergy antigen protein may be a protein of about 17 kDa (e.g., from 14 kDa to 20 kDa) secreted by *Malassezia globosa* to the outside of the fungus body. For example, the sweat allergy antigen protein may be a protein encoded by an MGL_1304 gene (e.g., a protein consisting of the amino acid sequence represented by SEQ ID NO: 1). The amino acid sequence represented by SEQ ID NO: 1 is as follows:

```
SEQ ID NO: 1:
MVSLNIFSAAFVASLASAVFAAPSALERRAAPDNTVWVTSVADHCLILPR

HKMSVGDSESPGNMRSFCTKPYSSKQGQLASDFWTKAHFKKTDKYVQITG

CINPNVQSTLLSNDEGGQYDSNGGEGGRGNPAGSVCLGYSSYVELVEPAG

NRACIRCCYDPSDCDVSQDEAGCETVIPGKYDC.
```

The sweat allergy antigen has histamine release activity. The histamine release activity can be measured in accordance with a known method (Koro, O. et al., J. Allergy Clin. Immunol., 103, 663-670, 1999). For example, the histamine release activity may be determined by contacting a sweat allergy antigen and an IgE antibody with cells expressing an IgE receptor on the cell surface and measuring the amount of histamine secreted from the cells. Examples of cells expressing an IgE receptor on the cell surfaces include basophils, mast cells, and a cell line being able to release a chemical transmitter such as histamine that is artificially prepared to express an IgE receptor gene.

For example, when the amount of histamine is measured and the amount of free histamine is in the range of 3 to 97% relative to the total amount of histamine, it can be determined that the histamine release activity is positive (Koro, O. et al., J. Allergy Clin. Immunol., 103, 663-670, 1999).

A human IgE antibody that does not induce degranulation in a reaction with a sweat allergy antigen protein may be a human IgE antibody that does not cause extracellular release of intragranular substances such as histamine and enzymes when the human IgE antibody contacts with cells expressing a high-affinity IgE receptor, such as mast cells or basophils, in the presence of the sweat allergy antigen protein.

The human IgE antibody is a human antibody and may be a polyclonal antibody or a monoclonal antibody. The human IgE antibody or an antibody fragment thereof may be labeled by an enzyme (e.g., Horseradish Peroxidase, biotin).

As used herein, an antibody fragment is a portion of an antibody that specifically binds to an antigen. Examples of antibody fragments include Fab (fragment of antigen binding), F(ab')2, Fab', a single-chain antibody (single chain Fv; hereinafter referred to as scFv), a disulfide stabilized antibody (disulfide stabilized Fv; hereinafter referred to as dsFv), a dimerized V-region fragment (hereinafter referred to as a diabody), and a peptide comprising CDR (Expert Opinion on Therapeutic Patents, Vol. 6, No. 5, pp. 441-456, 1996). The antibody and antibody fragment can be prepared by a well-known method in the art (see, e.g., Antibodies: A Laboratory Manual, Cold Spring Harbor Laboratory Press, 1988; gene.mie-u.ac.jp/Protocol/Original/Antibody.html; U.S. Pat. Nos. 6,331,415, 5,693,761, 5,225,539, 5,981,175, 5,612,205, 5,814,318, 5,545,806, 7,145,056, 6,492,160, 5,871,907, and 5,733,743).

The present inventors found that IgE monoclonal antibody (clone HE1) (DIA HE1-01A/DIA HE1-1A) (also referred to as ABS IgE antibody) purchasable from ABS is a human IgE antibody that binds to a sweat allergy antigen protein and a human high-affinity IgE receptor but does not induce degranulation in a reaction with the sweat allergy antigen protein.

In one embodiment, the human IgE antibody or antibody fragment that binds to a sweat allergy antigen protein and a human high-affinity IgE receptor but does not induce degranulation in a reaction with the sweat allergy antigen protein may be IgE monoclonal antibody (clone HE1) (DIA HE1-01A/DIA HE1-1A) purchasable from ABS or an antibody fragment thereof. The IgE monoclonal antibody (clone HE1) (DIA HE1-01A/DIA HE1-1A) is used as non-specific human IgE (diatec.com, Oslo, Norway) in Fairley J. A., et al., (2007) J. Invest. Dermatol. 127:2605-2611.

The IgE monoclonal antibody (clone HE1) (Catalog Number: DIA HE1-01A/DIA HE1-1A) is an IgE monoclonal antibody derived from a healthy person.

Accordingly, it was reasonably demonstrated that "a human IgE antibody that binds to a sweat allergy antigen protein and a human high-affinity IgE receptor but does not induce degranulation in a reaction with the sweat allergy antigen protein" can be isolated from an IgE antibody expression library derived from a healthy person, rather than a sweat allergy patient. Therefore, in one embodiment, the present invention provides a method of screening a human IgE antibody that binds to a sweat allergy antigen protein and a human high-affinity IgE receptor but does not induce degranulation in a reaction with the sweat allergy antigen protein from an IgE antibody expression library derived from a healthy person.

It is reported that a human IgE monoclonal antibody and a fragment thereof can be screened by using a phage display method (e.g., Steinberger P. et al., (1996) J. Biol. Chem. 271, 10967-10972).

For example, a human IgE monoclonal antibody having a desired bioactivity may be obtained by preparing a human IgE naive (i.e., non-immunized) library using filamentous phages such as M13 that express proteins from total RNA extracted from human IgE producing cells, and screening the library by panning.

Therefore, in one embodiment, the present invention provides a method of screening a human IgE antibody that binds to a sweat allergy antigen protein and a human high-affinity IgE receptor but does not induce degranulation with the sweat allergy antigen, comprising the steps of:

a) preparing a scFv phage library that is a naive (non-immunized) library by using RNA extracted from IgE producing cells of a healthy person;
b) screening and isolating a phage expressing scFv that binds to a sweat allergy antigen protein from the library;
c) amplifying VH and VL genes by PCR from the phage isolated in step b) to prepare an IgE antibody that binds to the sweat allergy antigen protein; and
d) reacting the IgE antibody prepared in step c) with mast cells or basophils in the presence of the sweat allergy antigen protein to isolate an IgE antibody that does not induce degranulation.

A specific example of the method of screening "a human IgE antibody or an antibody fragment thereof that binds to a sweat allergy antigen protein and a human high-affinity IgE receptor but does not induce degranulation with the sweat allergy antigen" may be a method comprising, but not limited to, the following steps:

step 1: preparing peripheral blood monocytes of a healthy person;
step 2: isolating mRNA to synthesize cDNA;
step 3: amplifying VH and VL genes, respectively, from the cDNA by PCR;
step 4: randomly linking the amplified VH and VL genes (e.g., randomly linking the amplified VH and VL genes by assembly PCR using an linker DNA which encodes a linker peptide sequence such as $(GGGGS)_3$) to prepare scFv genes;
step 5: incorporating the scFv genes thus prepared into a phagemid vector (e.g., pCANTAB5E) to establish an scFv gene library;
step 6: transforming *E. coli* with the scFv gene library thus prepared followed by co-infection with a helper phage to prepare an scFv phage library;
step 7: adding the scFv phage library to an immobilized sweat allergy antigen protein, removing unbound phages by washing, eluting bound phages, and infecting *E. coli* with the eluted phages to amplify the phages, and then isolating a phage expressing scFv specific to the sweat allergy antigen protein after repeating the aforementioned process several times;
step 8: amplifying VH and VL genes of the scFv specific to the sweat allergy antigen protein from the isolated phage by PCR, introducing the genes into a plasmid vector into which genes of constant region of an antibody have been incorporated, and then expressing the genes in animal cells such as CHO cells so as to prepare a monoclonal antibody that binds to the sweat allergy antigen protein;
step 9: contacting the monoclonal antibody thus prepared, which binds to the sweat allergy antigen protein, with cells expressing a high-affinity IgE receptor such as mast cells and basophils in the presence of the sweat allergy antigen protein to measure histamine release activity, and then isolating a monoclonal antibody lacking the histamine release activity as "a human IgE antibody that binds to a sweat allergy antigen protein and a human high-affinity IgE receptor but does not induce degranulation with the sweat allergy antigen". In this embodiment, primers used in PCR can be designed as appropriate by those skilled in the art (e.g., Steinberger P. et al., (1996) J. Biol. Chem. 271, 10967-10972).

In one embodiment, the present invention provides a method of manufacturing a human IgE antibody that binds to a human high-affinity IgE receptor but does not induce degranulation with the sweat allergy antigen, comprising the step of culturing an animal cell (e.g., CHO cell) that expresses a gene encoding the human IgE antibody isolated by the screening method as described above.

In one embodiment, "a human IgE antibody or an antibody fragment that binds to a sweat allergy antigen protein and a human high-affinity IgE receptor but does not induce degranulation in a reaction with the sweat allergy antigen protein" provided by the present invention may be a human IgE antibody or an antibody fragment thereof isolated from a human IgE expression library prepared from RNA of IgE producing cells of a healthy person.

2. Composition for Treatment of Sweat Allergy or Disease Related to Sweat Allergy Antigen, Composition for Removal or Neutralization of Sweat Allergy Antigen, or Material for Removal of Sweat Allergy Antigen In a second aspect, the present invention provides a composition for treatment of sweat allergy or a disease related to a sweat allergy antigen, a composition for removal or neutralization of a sweat allergy antigen, or a material for removal of a sweat allergy antigen, which comprises a human IgE antibody or an antibody fragment thereof that binds to a sweat allergy antigen protein and a human high-affinity IgE receptor but does not induce degranulation in a reaction with the sweat allergy antigen protein.

The IgE monoclonal antibody provided by the present invention is a human IgE that binds to a sweat allergy antigen protein and also stably binds to (sensitizes) a high-affinity IgE but does not induce degranulation from mast cells and basophils sensitized by this monoclonal antibody. This IgE monoclonal antibody may be the antibody provided in the first aspect of the present invention and may be, but not limited to, the IgE monoclonal antibody (clone HE1) purchasable from ABS, for example.

Therefore, a composition comprising the IgE monoclonal antibody (clone HE1) or an antibody fragment thereof may be used for treatment of sweat allergy or a disease related to a sweat allergy antigen.

As used herein, the disease related to a sweat allergy antigen may be a disease accompanied by sweat allergy induced by an antigenic substance contained in sweat and includes, for example, atopic dermatitis, urticaria (e.g., cholinergic urticaria), and allergic rhinitis.

The composition for treatment provided by the present invention is appropriately formulated by using the antibody provided in the first aspect of the present invention (e.g., IgE monoclonal antibody (clone HE1) purchasable from ABS). For example, the composition for treatment provided by the present invention can be formulated with pharmaceutically acceptable carriers (including additives). Examples of the pharmaceutically acceptable carriers include, but not limited to, excipients (e.g., dextrin, hydroxypropyl cellulose, and polyvinylpyrrolidone), disintegrators (e.g., carboxymethyl cellulose), lubricants (e.g., magnesium stearate), surfactants (e.g., sodium lauryl sulfate), solvents (e.g., water, saline, and soybean oil), and preservatives (e.g., p-hydroxybenzoic acid ester).

The dosage and administration method of the composition for treatment may appropriately be selected by those skilled in the art depending on age, body weight, and health condition of the subject. For example, the human IgE antibody or an antibody fragment thereof that binds to a sweat allergy antigen protein and a human high-affinity IgE receptor but does not induce degranulation in a reaction with the sweat allergy antigen protein may be administrated at 0.1 µg/kg body weight to 10 mg/kg body weight and may intravenously be administered at 0.1 to 100 mg per day for an human adult, for example.

An antibody that specifically binds to a sweat allergy antigen protein (e.g., IgE monoclonal antibody (clone HE1) purchasable from ABS) or an antibody fragment thereof can be used for neutralizing the antigen activity of the sweat allergy antigen. The antibody also can be used for removing the sweat allergy antigen from an affected part.

For example, an isotonic solution such as saline containing an antibody that specifically binds to a sweat allergy antigen protein or an antibody fragment thereof may be contacted with an affected part to neutralize the sweat allergy antigen and/or to achieve removal of the sweat allergy antigen from the affected part.

The composition for removal or neutralization of a sweat allergy antigen provided by the present invention is appropriately formulated by using the antibody provided in the first aspect of the present invention (e.g., IgE monoclonal antibody (clone HE1) purchasable from ABS). For example, a liquid composition may be prepared that contains 0.01 mg/ml to 10 mg/ml of a human IgE antibody or an antibody fragment thereof that binds to a sweat allergy antigen protein and a human high-affinity IgE receptor but does not induce degranulation in a reaction with the sweat allergy antigen protein.

An antibody that specifically binds to a sweat allergy antigen protein (e.g., IgE monoclonal antibody (clone HE1) purchasable from ABS) may be immobilized to fibers to prepare a material for removal of the sweat allergy antigen from an affected part. Examples of the materials include a wiping sheet. The material for removal of a sweat allergy antigen can appropriately be manufactured by those skilled in the art.

For example, Japanese Patent No. 3642340 discloses a method of manufacturing a material for removal such as a wiping sheet, comprising immobilizing an antibody to fibers (woven fabric or nonwoven fabric) with an official moisture regain of 7% or more.

Examples of methods of immobilizing an antibody to a carrier such as fibers include a method in which after the carrier is silanized using γ-aminopropyltriethoxysilane etc., an aldehyde group is introduced to a carrier surface by means of glutaraldehyde etc. to covalently bind the aldehyde group and the antibody; a method in which an untreated carrier is immersed in an aqueous solution of the antibody to immobilize the antibody to the carrier though ion binding; a method in which an aldehyde group is introduced to a carrier having a certain functional group to covalently bind the aldehyde group and the antibody; a method in which the antibody is subjected to ion-binding to a carrier having a certain functional group; and a method in which after a carrier is coated with a polymer having a certain functional group, an aldehyde group is introduced to covalently bind the aldehyde group and the antibody. The certain functional group as described above may be an NHR group (R is an alkyl group of any of methyl, ethyl, propyl, and butyl other than H), an NH2 group, a C6H5NH2 group, a CHO group, a COOH group, and an OH group. The antibody may be supported via a linker by the carrier, and examples of linkers to be used include maleimide, NHS (N-Hydroxysuccinimidyl) ester, imidoester, EDC (1-Etyl-3-[3-dimetylaminopropyl]carbodiimido), and PMPI (N-[p-Maleimidophenyl]isocyanete).

The material for removal may be impregnated with water containing glycerol to be stored.

In one embodiment, the present invention provides use of an human IgE antibody or an antibody fragment thereof that binds to a sweat allergy antigen protein and a human high-affinity IgE receptor but does not induce degranulation in a reaction with the sweat allergy antigen protein (e.g., IgE monoclonal antibody (clone HE1) purchasable from ABS) for manufacturing a composition for treatment of sweat allergy or a disease related to a sweat allergy antigen, a composition for removal or neutralization of a sweat allergy antigen, or a material for removal of a sweat allergy antigen.

In one embodiment, the present invention provides a method of treating sweat allergy or a disease related to a sweat allergy antigen comprising administering a human IgE antibody that binds to a sweat allergy antigen protein and a human high-affinity IgE receptor but does not induce degranulation in a reaction with the sweat allergy antigen protein (e.g., IgE monoclonal antibody (clone HE1) purchasable from ABS) or an antibody fragment thereof.

The present invention also provides a method of neutralization or removal of a sweat allergy antigen protein comprising contacting a sweat allergy antigen protein with a human IgE antibody that binds to a sweat allergy antigen protein and a human high-affinity IgE receptor but does not induce degranulation in a reaction with the sweat allergy antigen protein (e.g., IgE monoclonal antibody (clone HE1) purchasable from ABS) or an antibody fragment thereof.

3. Composition or Kit for Detection of Human Sweat Allergy Antigen Protein or for Measurement of Amount of Human Sweat Allergy Antigen Protein In a third aspect, the present invention provides a composition or kit for detection of a human sweat allergy antigen protein or for measurement of the amount of a human sweat allergy antigen protein, comprising a human IgE antibody or an antibody fragment thereof that binds to a sweat allergy antigen protein and a human high-affinity IgE receptor but does not induce degranulation in a reaction with the sweat allergy antigen protein.

The human IgE antibody that binds to a sweat allergy antigen protein and a human high-affinity IgE receptor but does not induce degranulation in a reaction with the sweat allergy antigen protein may be the antibody provided in the first aspect of the present invention and may be, but not limited to, IgE monoclonal antibody (clone HE1) purchasable from ABS, for example.

The detection of a sweat allergy antigen protein and the measurement of the amount of a sweat allergy antigen can be conducted by any method. For example, the detection of a sweat allergy antigen protein and the measurement of the amount of a sweat allergy antigen can be performed by Western blotting or ELISA.

Therefore, in one embodiment, the composition for detection of a human sweat allergy antigen protein or for measurement of the amount of a human sweat allergy antigen may be a composition comprising a human IgE antibody that binds to a sweat allergy antigen protein and a human high-affinity IgE receptor but does not induce degranulation in a reaction with the sweat allergy antigen protein (e.g., IgE monoclonal antibody (clone HE1) purchasable from ABS) or an antibody fragment thereof, for use in Western blotting or ELISA.

In one embodiment, the kit for detection of a human sweat allergy antigen protein or for measurement of the amount of a human sweat allergy antigen may be a kit comprising reagents necessary for Western blotting or ELISA. Examples of reagents necessary for Western blotting include an SDS-PAGE gel, a nitrocellulose membrane or PVDF membrane, a human IgE antibody that binds to a sweat allergy antigen protein and a human high-affinity IgE receptor but does not induce degranulation in a reaction with the sweat allergy antigen protein (e.g., IgE monoclonal antibody (clone HE1) purchasable from ABS) or an antibody fragment thereof, a blocking solution (e.g., BSA solution, milk protein solution), a washing solution (phosphate buffer solution containing a surfactant (e.g., PBS containing Tween20)), and a luminescence detection reagent. Examples of reagents necessary for ELISA include a plate (e.g., a 96-well plate), a human IgE antibody that binds to a sweat allergy antigen protein and a human high-affinity IgE receptor but does not induce degranulation in a reaction with the sweat allergy antigen protein (e.g., IgE monoclonal antibody (clone HE1) purchasable from ABS) or an antibody fragment thereof, a blocking solution (e.g., BSA solution, milk protein solution), a washing solution (phosphate buffer solution containing a surfactant (e.g., PBS containing Tween20)), and a chromogenic substrate (e.g., TMB).

ELISA may be performed using a human sweat allergy antigen protein directly immobilized on an ELISA plate and "a human IgE antibody or an antibody fragment thereof that binds to a sweat allergy antigen protein and a human high-affinity IgE receptor but does not induce degranulation in a reaction with the sweat allergy antigen protein" as a detection antibody. ELISA may be sandwich ELISA using, for example, "a human IgE antibody or an antibody fragment thereof that binds to a sweat allergy antigen protein and a human high-affinity IgE receptor but does not induce degranulation in a reaction with the sweat allergy antigen protein" along with a different antibody that specifically binds to a sweat allergy antigen protein (e.g., a protein consisting of the amino acid sequence represented by SEQ ID NO: 1) or an antibody fragment thereof. Examples of different antibodies that specifically bind to a sweat allergy antigen protein (e.g., a protein consisting of the amino acid sequence represented by SEQ ID NO: 1) include, but not limited to, a monoclonal antibody or a polyclonal antibody prepared by immunizing a mammal (e.g., rat or rabbit) with the protein consisting of the amino acid sequence represented by SEQ ID NO: 1. The monoclonal antibody may be any one of the following (i) to (iii):

(i) antibody produced by the hybridoma of Accession No. FERM BP-11110 deposited to the International Patent Organism Depositary of the National Institute of Advanced Industrial Science and Technology (address: Central 6, 1-1-1 Higashi, Tsukuba, Ibaraki, Japan (postal code: 305-8566)) on Apr. 1, 2009 (transferred from FERM P-21439 deposited on Nov. 16, 2007) (Mouse-Mouse hybridoma smith-1) (also referred to as Smith1 antibody in this description);

(ii) antibody produced by the hybridoma of Accession No. FERM BP-11111 deposited to the International Patent Organism Depositary of the National Institute of Advanced Industrial Science and Technology (address: Central 6, 1-1-1 Higashi, Tsukuba, Ibaraki, Japan (postal code: 305-8566)) on Apr. 1, 2009 (transferred from FERM P-21440 deposited on Nov. 16, 2007) (Mouse-Mouse hybridoma smith-2) (also referred to as Smith2 antibody in this description); and (iii) antibody produced by the hybridoma of Accession No. FERM BP-11112 deposited to the International Patent Organism Depositary of the National Institute of Advanced Industrial Science and Technology (address: Central 6, 1-1-1 Higashi, Tsukuba, Ibaraki, Japan (postal code: 305-8566)) on Apr. 1, 2009 (transferred from FERM P-21697 deposited on Oct. 1, 2008) (Mouse-Mouse hybridoma smith-8) (also referred to as Smith8 antibody in this description).

Therefore, in one embodiment, the present invention provides an ELISA kit for detection of a human sweat allergy antigen protein or for measurement of the amount of a human sweat allergy antigen, comprising:

(1) a human IgE antibody that binds to a sweat allergy antigen protein and a human high-affinity IgE receptor but does not induce degranulation in a reaction with the sweat allergy antigen protein (e.g., IgE monoclonal antibody (clone HE1) purchasable from ABS) or an antibody fragment thereof; and (2) a monoclonal or polyclonal antibody prepared by immunizing a mammal (e.g., rat or rabbit) with the protein consisting of the amino acid sequence represented by SEQ ID NO: 1 (e.g., Smith1 antibody, Smith2 antibody, or Smith8 antibody) or an antibody fragment thereof.

The human IgE antibody (e.g., IgE monoclonal antibody (clone HE1) purchasable from ABS) or antibody fragment thereof as described in (1) and the monoclonal or polyclonal antibody prepared by immunizing a mammal (e.g., rat or rabbit) with the protein consisting of the amino acid sequence represented by SEQ ID NO: 1 (e.g., Smith1 antibody, Smith2 antibody, or Smith8 antibody) or antibody fragment thereof as described in (2) may be used as an immobilized antibody and as a detection antibody. For example, the Smith2 antibody may be immobilized and the IgE monoclonal antibody (clone HE1) purchasable from ABS may be used as a detection antibody for for detecting a human sweat allergy antigen bound to the immobilized Smith2 antibody.

The kit for detection of a human sweat allergy antigen protein or for measurement of the amount of a human sweat allergy antigen provided in the third aspect by the invention may include, as a standard substance, a protein encoded by MGL_1304 gene (e.g., the protein consisting of the amino acid sequence represented by SEQ ID NO: 1), or a protein that is present in a culture supernatant of *Malassezia globosa* and binds to serum derived from a sweat allergy patient and/or Smith2 antibody, or a protein that is obtained by partial purification from human sweat by a known method and binds to serum derived from a sweat allergy patient and/or Smith2 antibody. By using a solution comprising at a known concentration a protein encoded by MGL_1304 gene (e.g., the protein consisting of the amino acid sequence represented by SEQ ID NO: 1) or a protein that is present in a culture supernatant of *Malassezia globosa* and binds to serum derived from a sweat allergy patient and/or Smith2 antibody, the amount of a sweat allergy antigen can be accurately quantified. For example, by using solutions each comprising a known concentration of a protein that is present in a culture supernatant of *Malassezia globosa* and binds to serum derived from a sweat allergy patient and/or Smith2 antibody, the amount of a sweat allergy antigen can accurately be quantified.

Western blotting and ELISA can be conducted as appropriate by those skilled in the art.

For example, in Western blotting, a sample containing a sweat allergy antigen is separated by electrophoresis in a SDS-PAGE gel, and transcribed to a PVDF membrane. The membrane is reacted with "a human IgE antibody that binds to a sweat allergy antigen protein and a human high-affinity IgE receptor but does not induce degranulation in a reaction with the sweat allergy antigen protein or an antibody fragment thereof" (e.g., IgE monoclonal antibody (clone HE1) purchasable from ABS) and then with an enzyme-labeled anti-human IgE antibody. After that, the sweat allergy antigen can be detected or quantified based on the enzyme activity.

The composition or kit provided in the third aspect of the present invention is appropriately formulated by using the antibody provided in the first aspect of the present invention (e.g., IgE monoclonal antibody (clone HE1) purchasable from ABS). For example, a liquid composition or kit may be prepared that comprises 0.01 mg/ml to 10 mg/ml of a human IgE antibody or an antibody fragment thereof that binds to a sweat allergy antigen protein and a human high-affinity IgE receptor but does not induce degranulation in a reaction with the sweat allergy antigen protein.

In one embodiment, the present invention provides use of a human IgE antibody or an antibody fragment thereof that binds to a sweat allergy antigen protein and a human high-affinity IgE receptor but does not induce degranulation in a reaction with the sweat allergy antigen protein (e.g., IgE monoclonal antibody (clone HE1) purchasable from ABS), for manufacturing a composition or kit for detection of a human sweat allergy antigen protein or for measurement of the amount of a human sweat allergy antigen protein.

In one embodiment, the present invention provides a method of detection of a human sweat allergy antigen protein, a method of measurement of the amount of a human sweat allergy antigen protein, or a method of diagnosis of sweat allergy or a disease related to a sweat allergy antigen, comprising contacting a human-derived sample with "a human IgE antibody that binds to a sweat allergy antigen protein and a human high-affinity IgE receptor but does not induce degranulation in a reaction with the sweat allergy antigen protein (e.g., IgE monoclonal antibody (clone HE1)" or an antibody fragment thereof. The method may be performed in vitro.

The human-derived sample may be a sample containing a human sweat allergy antigen protein and may be, for example, sweat collected from a human (e.g., sweat collected from a sweat allergy patient), skin washing (e.g., a solution obtained by washing skin of a sweat allergy patient with saline), horny layer of human body surface (e.g., cubital fossa, upper arm, neck), serum, or plasma.

4. Composition or Kit for Detection of Antibody that Binds to Human Sweat Allergy Antigen Protein or for Measurement of Amount of Antibody that Binds to Human Sweat Allergy Antigen Protein In a fourth aspect, the present invention provides a composition or kit for detection of an antibody that binds to a human sweat allergy antigen protein, or for measurement of the amount of an antibody that binds to a human sweat allergy antigen protein, comprising a standard substance, wherein the standard substance is a human IgE antibody that binds to a sweat allergy antigen protein and a human high-affinity IgE receptor but does not induce degranulation in a reaction with the sweat allergy antigen protein.

As used herein, a standard substance is a substance that acts as a positive control when a certain substance is detected or quantified. In one embodiment, when a certain substance is quantified with a standard substance, the result of quantification can be represented in an absolute concentration (e.g., pg/ml) of the standard substance.

In the fourth aspect of the present invention, "a human IgE antibody that binds to a sweat allergy antigen protein and a human high-affinity IgE receptor but does not induce degranulation in a reaction with the sweat allergy antigen protein" used as a standard substance may be the antibody provided in the first aspect of the present invention and is preferably a monoclonal antibody. For example, the antibody may be, but not limited to, the IgE monoclonal antibody (clone HE1) purchasable from ABS, for example.

Examples of antibodies that bind to a human sweat allergy antigen protein to be detected or measured in amount in the fourth aspect of the invention include a human IgE antibody, a human IgG antibody, a human IgA antibody, a human IgD antibody, and a human IgM antibody. These antibodies that bind to a human sweat allergy antigen protein can be detected or measured by any method and may be detected or measured by ELISA or Western blotting, for example.

Therefore, the composition or kit provided in the fourth aspect of the present invention may be for ELISA or Western blotting.

ELISA for detection or measurement of a human IgE antibody, a human IgG antibody, a human IgA antibody, a human IgD antibody, or a human IgM antibody that binds to a human sweat allergy antigen protein may be designed as appropriate by those skilled in the art. For example, the detection or measurement of a human IgG antibody, a human IgA antibody, a human IgD antibody, or a human IgM antibody that binds to a human sweat allergy antigen protein can be performed by using an ELISA system in which the IgE monoclonal antibody (clone HE1) purchasable from ABS is immobilized, a human sweat allergy antigen protein is added to bind to the immobilized antibody, and then a human antibody (e.g., IgG antibody in human serum) bound to the human sweat allergy antigen protein is detected by an HRP-labeled anti-human immunoglobulin (e.g., IgG) antibody. For example, the detection or measurement of a human IgE antibody that binds to a human sweat allergy antigen protein can be performed by using an ELISA system in which a Fab fragment, Fab' fragment, or F(ab')2 fragment of the IgE monoclonal antibody (clone HE1) purchasable from ABS is immobilized, a human sweat allergy antigen protein is added to bind to the immobilized fragment, and then a human IgE antibody (e.g., IgE antibody in human serum) bound to the human sweat allergy antigen protein is detected by an HRP-labeled anti-human IgE antibody specifically recognizing the FC portion of IgE.

Therefore, in one embodiment, the present invention provides use of a human IgE antibody or an antibody fragment thereof that binds to a sweat allergy antigen protein and a human high-affinity IgE receptor but does not induce degranulation in a reaction with the sweat allergy antigen protein (e.g., the IgE monoclonal antibody (clone HE1) purchasable from ABS), for manufacturing a composition or kit for detection of an antibody that binds to a human sweat allergy antigen protein or for measurement of the amount of an antibody that binds to a human sweat allergy antigen protein.

Human serum may contain an antibody such as human IgG or IgE that recognizes mouse IgG (Human Anti-Mouse Antibody: HAMA). Thus, ELISA comprising mouse IgG as a constituent requires a process for removing HAMA from such serum in advance. However, the removal of HAMA is not required when "a human IgE antibody or antibody fragment thereof that binds to a sweat allergy antigen protein and a human high-affinity IgE receptor but does not induce degranulation in a reaction with the sweat allergy antigen protein" (e.g., the IgE monoclonal antibody (clone HE1) purchasable from ABS, a Fab fragment, a Fab' fragment, or a F(ab')2 fragment thereof) is used in the kit for detection of an antibody that binds to a human sweat allergy antigen protein or for measurement of the amount of an antibody binding to a human sweat allergy antigen protein provided in the fourth aspect by the present invention to immobilize the sweat allergy antigen protein on a solid support such as an ELISA plate.

By quantifying an antibody that binds to a human sweat allergy antigen protein by using the composition or kit provided in the fourth embodiment by the present invention, sweat allergy or a disease related to a sweat allergy antigen can be diagnosed.

For example, the amount of an antibody (e.g., IgE and/or IgG (all types of IgG and/or IgG4, for example)) that binds to a sweat allergy antigen in a blood sample (e.g., serum or plasma) of a human subject is measured by the kit provided in the fourth aspect of the present invention, and compared with the amount of the antibody in a blood sample of a healthy person. When the amount of the antibody in the blood sample of the subject is higher than the amount of the antibody in the blood sample of a healthy person, it can be diagnosed that the subject has sweat allergy or a disease related to sweat allergy antigens, or has a risk of sweat allergy or a disease related to sweat allergy antigens. Alternatively, the result of measurement of the amount of an antibody that binds to a sweat allergy antigen can be used to assist diagnosis of sweat allergy or a disease related to a sweat allergy antigen based on clinical findings. Further, when the concentration of an antibody that binds to a sweat allergy antigen in a blood sample is high in a patient diagnosed as having sweat allergy or a disease related to a sweat allergy antigen, it can be diagnosed that the treatment of removing the sweat allergy antigen protein and/or improving sweat allergy is more effective for the patient compared to a patient who has a low concentration of the antibody.

With regard to this example, when the IgE monoclonal antibody (clone HE1) purchasable from ABS is used as a standard substance to create a standard curve to quantify the antibody of a subject or a healthy person, the concentration of the antibody of a subject or a healthy person can be converted into the concentration (e.g., in pg/ml) of the IgE monoclonal antibody (clone HE1) purchasable from ABS, and the value can be compared with a corresponding value obtained at a different time. While the value primarily measured in ELISA is absorbance in general, comparison of test results conducted at different times is practically impossible because the absorbance is not constant in every test. In contrast, by using the human IgE antibody that binds to a sweat allergy antigen protein and a human high-affinity IgE receptor but does not induce degranulation in a reaction with the sweat allergy antigen protein (e.g., the IgE monoclonal antibody (clone HE1) purchasable from ABS) at a known concentration as a standard substance and by converting the test results into the concentrations of the standard substance, the test results conducted at different times can be compared in an objective manner.

The composition or kit provided by the fourth embodiment of the present invention is useful, for example, for determining the therapeutic effect of a hyposensitization therapy. For example, when the amount of the IgE antibody that binds to a sweat allergy antigen decreases and/or the amount of IgG4 antibody that binds to a sweat allergy antigens increases as a result of the hyposensitization therapy with the sweat allergy antigen for a sweat allergy patient, the hyposensitization therapy can be determined as effective.

Non-limiting examples of the kit provided in the fourth aspect of the present invention include:
(1) an ELISA kit comprising an ELISA plate, a sweat allergy antigen protein (e.g., MGL_1304 protein), an anti-human IgE antibody, and the IgE monoclonal antibody (clone HE1) purchasable from ABS at a known concentration as a standard substance (in this case, after the sweat allergy antigen protein (e.g., MGL_1304 protein) is immobilized on the ELISA plate, serum or plasma derived from a subject is added thereto concurrently with a known concentration of the IgE monoclonal antibody (clone HE1) purchasable from ABS, then the bound IgE antibody from the serum or plasma is detected with the anti-human IgE antibody); and
(2) an ELISA kit comprising an ELISA plate, Smith2 antibody (Accession No. FERM BP-11111), a composition comprising a sweat allergy antigen protein (e.g., a partially purified sweat antigen (QRX)), an anti-human IgE antibody, and the IgE monoclonal antibody (clone HE1) purchasable from ABS at a known concentration as a standard substance (in this case, after the Smith2 antibody is immobilized on the ELISA plate and the sweat allergy antigen protein (e.g., MGL_1304 protein) is added to bind to the immobilized Smith2 antibody, serum or plasma derived from a subject is added thereto concurrently with a known concentration of the IgE monoclonal antibody (clone HE1) purchasable from ABS, then the bound IgE antibody from the serum or plasma is detected with the anti-human IgE antibody).

The composition or kit provided in the fourth aspect of the present invention is appropriately formulated by using the antibody provided in the first aspect of the present invention (e.g., the IgE monoclonal antibody (clone HE1) purchasable from ABS). For example, a liquid composition or kit may be prepared that contains 0.01 µg/ml to 10 mg/ml of the human IgE antibody or an antibody fragment thereof that binds to a sweat allergy antigen protein and a human high-affinity IgE receptor but does not induce degranulation in a reaction with the sweat allergy antigen protein.

In one embodiment, the present invention provides use of "a human IgE antibody that binds to a sweat allergy antigen protein and a human high-affinity IgE receptor but does not induce degranulation in a reaction with the sweat allergy antigen protein (e.g., the IgE monoclonal antibody (clone HE1) purchasable from ABS)" or an antibody fragment thereof, as a standard substance in detection of an antibody, or measurement of the amount of an antibody that binds to a human sweat allergy antigen protein. The antibody or antibody fragment thereof may be used in vitro.

The present invention will hereinafter further be described in examples and these examples are not intended to limit the present invention.

EXAMPLES

Example 1: Purification of Partially Purified Sweat Antigen (QRX)

1-1. Preparation of Concentrated Sweat

After insolubles were removed from human sweat through 100-µm and 70-µm mesh filters (Nylon Cell Strainers, Falcon), precipitates were further removed by a 0.22-µm filter (Bottle Top Filter, 1 L, Corning). Four litters of the sweat filtrated by the filters were concentrated by ultrafiltration (3000M.W.cut) to about 150 mL and used as a material for the sweat antigen purification.

1-2. Separation by Anion-Exchange Column

To an anion-exchange column MonoQ 10/100 GT (GE Healthcare Bio-Sciences) preliminarily equilibrated with 10 mmol/L Tris-HCl (pH 8.0), 75 mL of the concentrated sweat prepared at pH 8.0 was loaded, and was eluted through 0 to 1.0 M NaCl concentration gradient in 10 mmol/L Tris-HCl (pH 8.0). AKTA Explorer (GE Healthcare Bio-Sciences) was used as a chromatographic device for purification.

To select a fraction containing a substance having a histamine release activity, a histamine release test using basophils of an atopic dermatitis patient was performed for each of fractions.

First, each of the appropriately diluted fractions was mixed at 1:1 with a basophil fraction of an atopic dermatitis patient prepared in a HEPES buffer containing 5 mmol/L glucose, 0.03 w/v % HSA, 2 mmol/L $CaCl_2$, and 1 mmol/L $MgCl_2$, and was incubated at 37° C. for 40 minutes. After supernatant and sedimented blood cells were separated by centrifugation and proteins were respectively denatured by adding 0.2 mol/L perchloric acid, a histamine concentration in the supernatant obtained by the centrifugation was measured by HPLC (Shimadzu LC solution). The percentage of the histamine amount of the supernatant relative to the total histamine amount was defined as a histamine release activity.

The histamine amount was measured in accordance with a method described in a literature (Koro, O. et al., J. Allergy Clin. Immunol., 103, 663-670, 1999).

A fraction eluted with the salt concentration range of 0.25 to 0.3 mol/L NaCl having a higher histamine release activity compared to the other fractions was recovered as a fraction exhibiting the histamine release activity, referred to as "QR fraction" herein after.

1-3. Separation by Reverse-Phase Column

After 18 mL of the fraction (QR) acquired in Example 1-2 is diluted with pure water 10 times, TFA was added at a final concentration of 0.1 v/v %. The solution was loaded to a reverse-phase column (SOURCE 15RPC ST 4.6/100 (GE Healthcare Bio-Sciences)) and was eluted through concentration gradient from 0.1 v/v % TFA/distilled water to 0.1 v/v % TFA/acetonitrile. AKTA Explorer (GE Healthcare Bio-Sciences) was used as a chromatographic device for purification.

After TFA and acetonitrile of the eluted fractions were volatilized, the histamine release test was performed as in Example 1-2.

A fraction eluted with the range of about 30 to 35 v/v % acetonitrile having a higher histamine release activity compared to the other fractions was recovered as a fraction exhibiting the histamine release activity (4 mL).

1-4. Separation by Gel Filtration Chromatography

After lyophilization, the fractions obtained in Example 1-3 were re-dissolved in PBS, loaded to Superdex 75 PC 3.2/30 (GE Healthcare Bio-Sciences), and fractionated and eluted in PBS (−). Smart System (GE Healthcare Bio-Sciences) was used as a chromatographic device for purification.

For each of the eluted fractions, the histamine release test was performed as in Example 1-2.

As a result, the range of elution positions from 15 to 60 kD was recovered as a fraction exhibiting the histamine release activity (1.2 mL) and subsequently defined as QRX fraction.

Example 2: Purification and Mass Spectrometry of Partially Purified Sweat Antigen (QRX)

Figure 1:
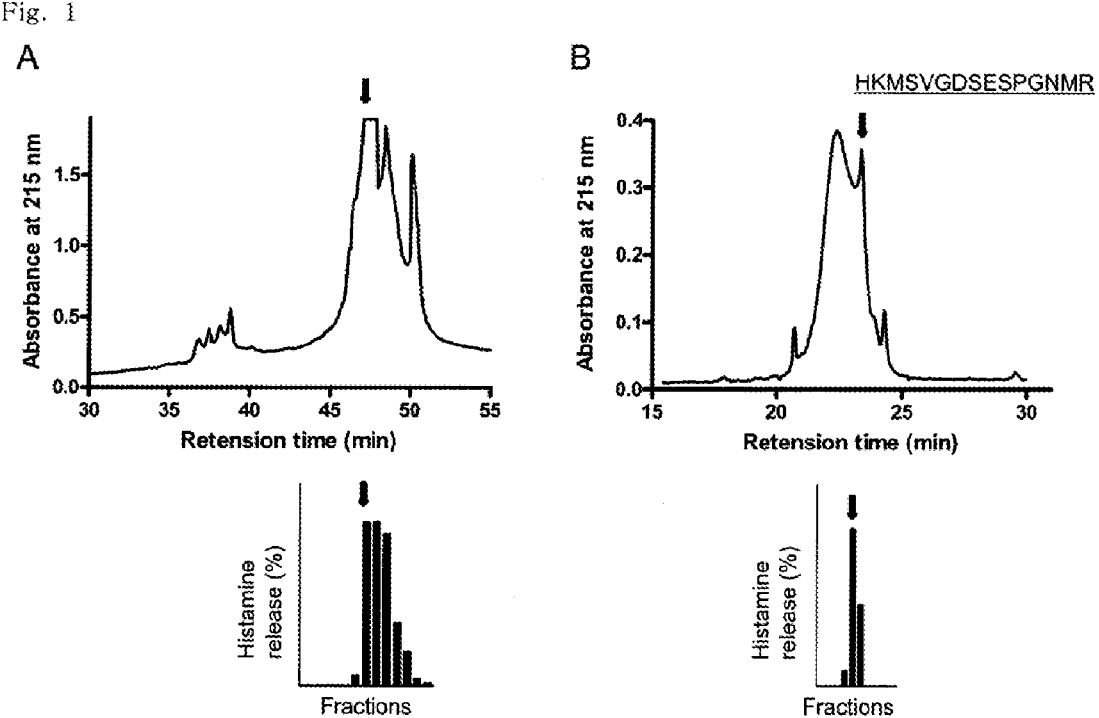
FIG. 1 shows that an amino acid sequence identical to MGL_1304 was detected by mass spectrometry after conducting further purification of partially purified sweat antigens (hereinafter also referred to as QRX).

The partially purified sweat antigen (QRX) was purified by using an Aqua 5μ-C18-200A HPLC column (manufactured by Phenomenex) (eluted through concentration gradient from 0.1 v/v % TFA/distilled water to 0.1 v/v % TFA/100% acetonitrile). The fraction exhibiting the histamine release activity was recovered and further purified by a Jupiter 5 μC18-300A HPLC column (manufactured by Phenomenex) (eluted through concentration gradient from 0.1 v/v % TFA/distilled water to 0.1 v/v % TFA/80% acetonitrile), and a mass spectrometry (TOF-MS) was performed for the fraction exhibiting the histamine release activity (fraction indicated by an arrow in FIG. 1). While a sample was generally cationized in TOF-MS, the mass measurement was performed through anionization in this experiment. The histamine release activity was measured in accordance with a method described in Koro, O. et al., J. Allergy Clin. Immunol., 103, 663-670, 1999. The detected amino acid sequence matched MGL_1304.

Figure 2:
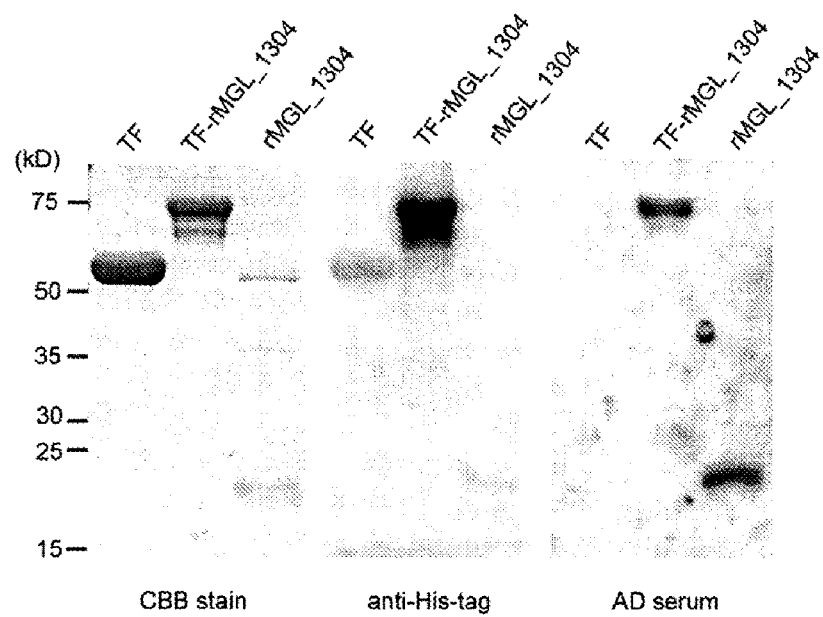
FIG. 2 shows CBB staining and Western blotting analysis of the recombinant protein using an atopic dermatitis patient serum and an anti-his tag antibody.

Example 3: Preparation of Recombinant Protein of MGL_1304 and Reactivity to Atopic Dermatitis Patient IgE Malassezia globosa was purchased from ATCC (MYA-4612). Reverse transcription of mRNA extracted from Malassezia globosa to cDNA was performed and cDNA encoding MGL_1304 was amplified by PCR (sense primer: 5'-GGGGTACCGTATCCCTCAACATTTTCTCAGCTGC-3' (SEQ ID NO: 2); antisense primer: 5'-CCCAAGCTTT-TAGCAGTCGTACTTGCCGGGGATG-3' (SEQ ID NO: 3), (94° C., 5 min/60° C., 1 min/72° C., 1 min)×1 cycle, (94° C., 1 min/60° C., 1 min/72° C., 1 min)×30 cycles, (94° C., 5 min/60° C., 1 min/72° C., 10 min)×1 cycle). The amplified cDNA was inserted into the p Cold TF vectors (manufactured by TAKARA BIO INC.) followed by transfection of E. coli JM109 with the obtained vector. After 24 hours culture at 15° C., the resulting E. coli was dissolved in xTractor buffer and a recombinant protein was purified by a cobalt column. Trigger Factor only (TF), a TF-MGL_1304 fusion protein (TF-MGL_1304), and a protein obtained by removal of TF from the fusion protein by enzyme treatment (rMGL_1304) were prepared. The obtained proteins were subjected to acrylamide gel electrophoresis and were directly CBB-stained (left side of FIG. 2) or transferred to PVDF membranes for immunoblotting with an anti-His tag antibody (center of FIG. 2) and an atopic dermatitis patient serum (right side of FIG. 2). As a result, the atopic dermatitis patient IgE bound to rMGL 1304 (FIG. 2).

Figure 3:
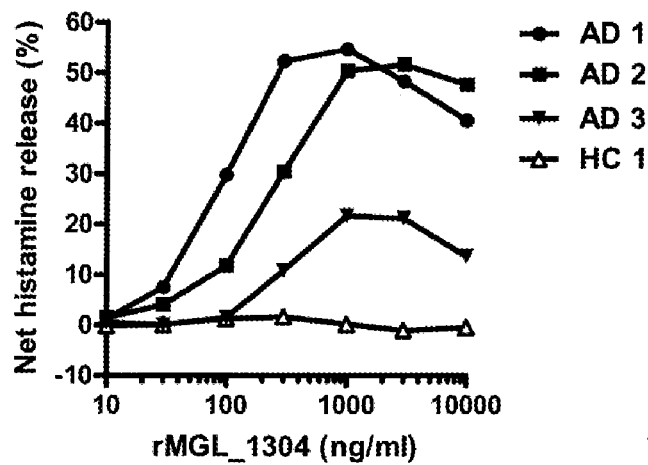
FIG. 3 shows a histamine release assay of atopic dermatitis patients (AD1, AD2, and AD3) and a healthy person (HC1) for the recombinant protein of MGL_1304.

The prepared rMGL_1304 was reacted with atopic dermatitis patient peripheral blood basophils (FIG. 3, AD1, AD2, and AD3) and healthy person peripheral blood basophils (FIG. 3, HCl) to perform the histamine release test. As a result, MGL_1304 induced histamine release specifically in the atopic dermatitis patients.

Figure 4:
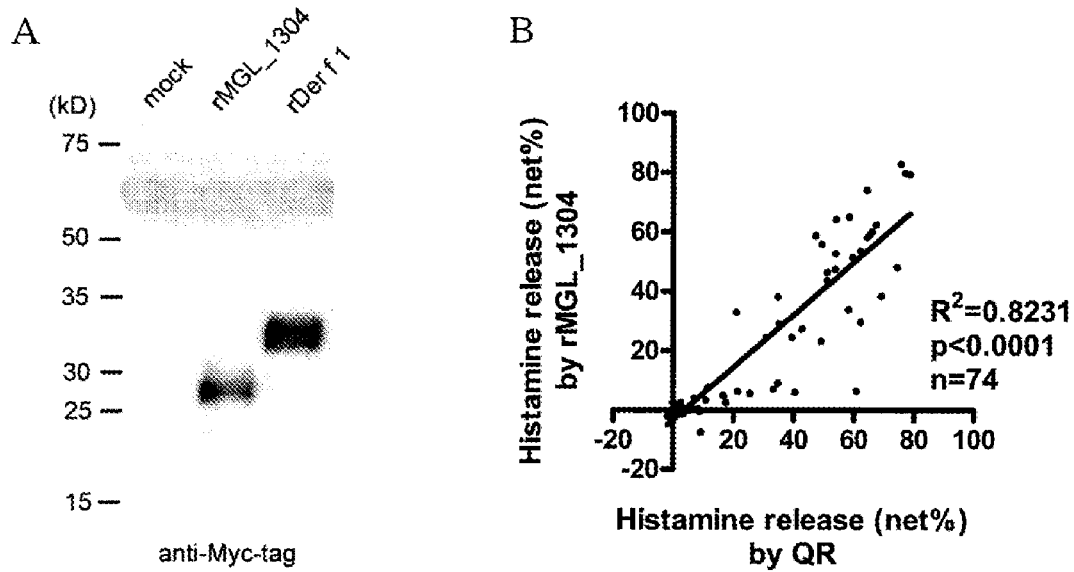
In FIG. 4, A shows the result of Western blotting in which an MGL_1304 gene or a mite antigen gene fused with Myc-tag was expressed in COS7 cells and culture supernatant of the cells was separated by electrophoresis and detected with an anti-Myc antibody.

Additionally, cDNA encoding the MGL_1304 described above or mite cDNA was inserted into pSecTag2/Hygro vector (manufactured by Invitrogen) containing Myc-tag and COS7 cells were transfected with the resulting vector. A culture supernatant of the COS7 cells transfected with these DNAs was subjected to acrylamide gel electrophoresis and transferred to a PVDF membrane for immunoblotting with anti-Myc tag antibodies. As a result, the culture supernatant contained proteins corresponding to respective cDNAs (A in FIG. 4). The culture supernatant was further reacted with atopic dermatitis patient peripheral blood basophils for the histamine release test. The same basophils were reacted with a sweat antigen partially purified from the concentrated human sweat by the anion-exchange column chromatography and the reverse-phase column chromatography (QR) and the histamine release test was performed, for comparison with the histamine release rate with the culture supernatant (B in FIG. 4).

As a result, MGL_1304 protein (rMGL 1304) produced by the COS7 cells induced histamine release similar to the partially purified human sweat antigen (QR).

Example 4: Reactivity Between Recombinant MGL_1304 Protein and Atopic Dermatitis Patient IgE It was studied whether MGL_1304 had substantially the same property as the partially purified sweat antigen (QRX) that has been used so far.

Figure 5:
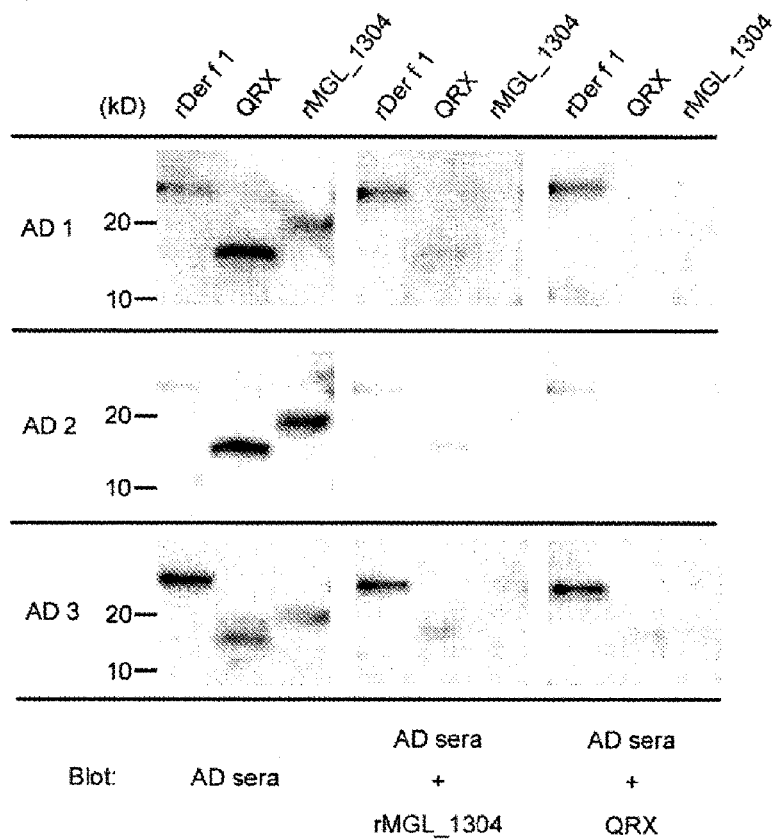
FIG. 5 shows that pretreatment of atopic dermatitis patient serums with one of QRX and MGL_1304 neutralizes the binding of antibody with the other one, respectively.

(1)
Recombinant mite antigen (Der f1), QRX, and MGL_1304 were electrophoresed and transferred to a plurality of PVDF membranes. An atopic patient serum (AD serum) pretreated with QRX or MGL_1304 prepared in Example 3 or AD serum without pretreatment was used for immunoblotting. The atopic dermatitis patient serums were obtained from three patients. The pretreatment with MGL_1304 inhibited the binding of IgE to QRX and the pretreatment with QRX inhibited the binding of IgE to MGL_1304 (FIG. 5).

Figure 6:
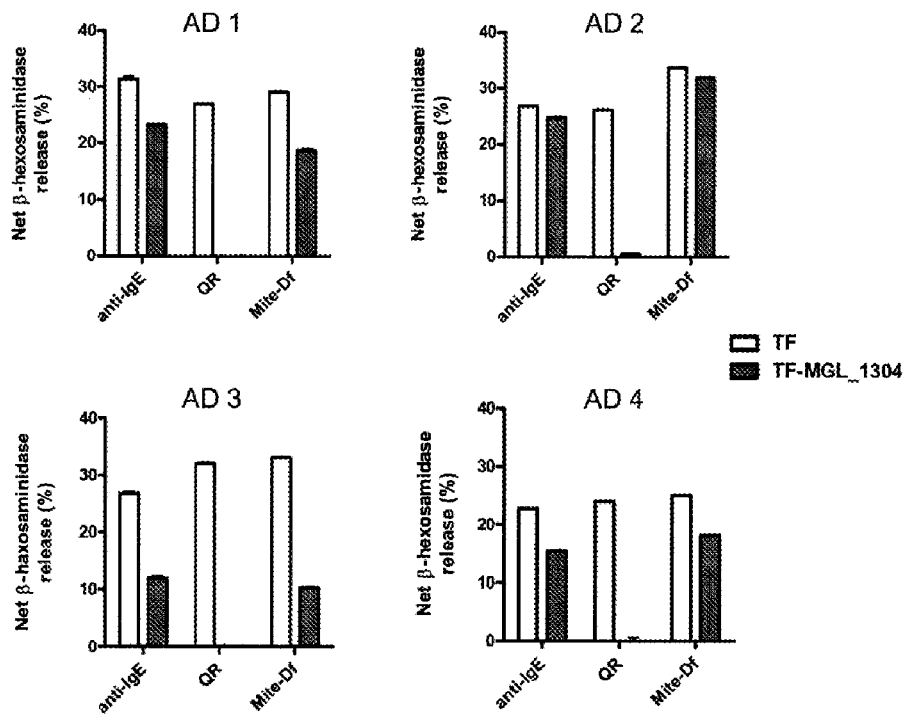
FIG. 6 shows that when the atopic dermatitis patient serum is reacted with a rat mast cell line expressing a human high-affinity IgE receptor to sensitize the cell (to provide sensitivity to the antigen), the reactivity (ability of histamine release) of the sensitized cell to QRX is disappeared by the pretreatment with MGL_1304.

(2)
The atopic dermatitis patient serums (AD1 to AD4) were pretreated with TF or TF-MGL_1304 and used for sensitization of a rat cell line expressing a human IgE receptor (sub-unit A), and the degranulation induced by the stimulation with an anti-human IgE antibody (anti-IgE), QRX, or a mite extract (Mite-DO was measured. As a result, when MGL_1304 specific IgE was removed by pretreatment with MGL_1304 prepared in Example 3, the reactivity to QRX stimulation disappeared (FIG. 6).

Example 5: Binding of Various Types of Human IgE to QRX

An ELISA plate was coated with QRX prepared in Example 1 (50 ng/well). For each of ABS human monoclonal IgE (non-immune) antibody (κ, derived from monoclonal hybridoma: ABS DIA HE1-01A/DIA HE1-1A) (also referred to as an ABS IgE antibody), CHEMICON human myeloma IgE antibody (CHEMICON=Millipore AG30P), AbD serotec human myeloma IgE antibody (λ: AbD serotec PHP142), and GenWay Biotech human myeloma IgE antibody (κ: GenWay Biotech 11-511-248640), concentration-dependent detection of QRX was studied by ELISA. The human IgE antibody that bound to QRX was detected with an HRP-labeled anti-human IgE antibody.

Figure 7:
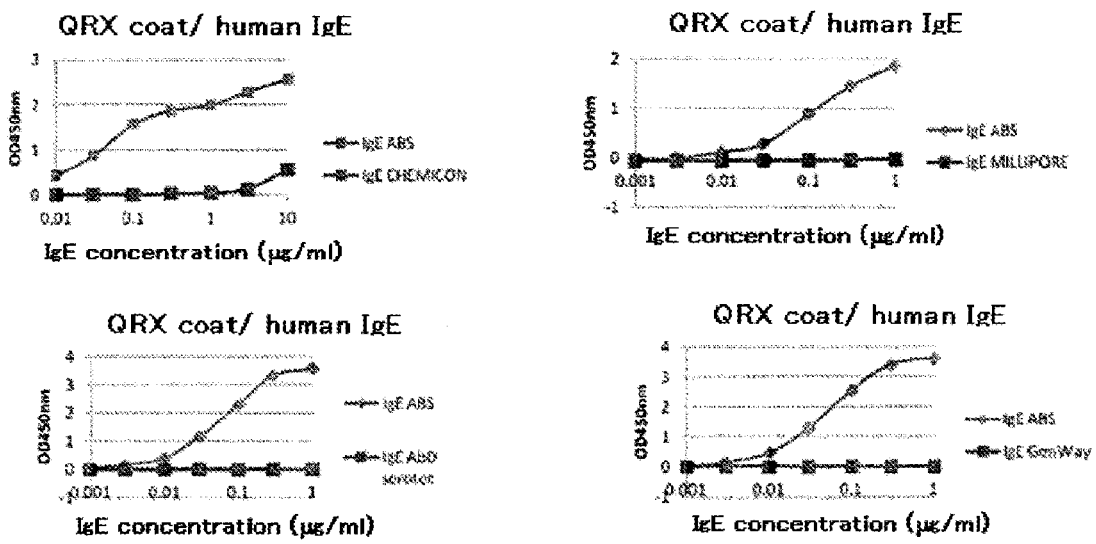
FIG. 7 shows the binding of the following human IgE antibodies to QRX: ABS human monoclonal IgE (non-immune) antibody (κ, derived from monoclonal hybridoma: ABS DIA HE1-01A/DIA HE1-1A) (hereinafter also referred to as ABS IgE antibody), CHEMICON human myeloma IgE antibody (CHEMICON=Millipore AG30P), AbD serotec human myeloma IgE antibody (λ: AbD serotec PHP142), and GenWay Biotech human myeloma IgE antibody (κ: GenWay Biotech 11-511-248640).

As a result, QRX was detected in a concentration-dependent manner only when the AB human monoclonal IgE antibody was used (FIG. 7). The results demonstrate that the ABS human monoclonal IgE antibody binds to QRX and can detect QRX quantitatively.

Example 6: Binding of ABS IgE Antibody to rMGL_1304

An ELISA plate was coated with the TF-MGL_1304 fusion protein prepared by forced expression from *E. coli* in Example 3 (150 ng/well). It was studied by ELISA whether the ABS IgE antibody and the CHEMICON human myeloma IgE antibody detect the TF-MGL_1304 fusion protein in a concentration dependent manner. The human IgE antibody binding to the TF-MGL_1304 fusion protein was detected with an HRP-labeled anti-human IgE antibody.

Figure 8:
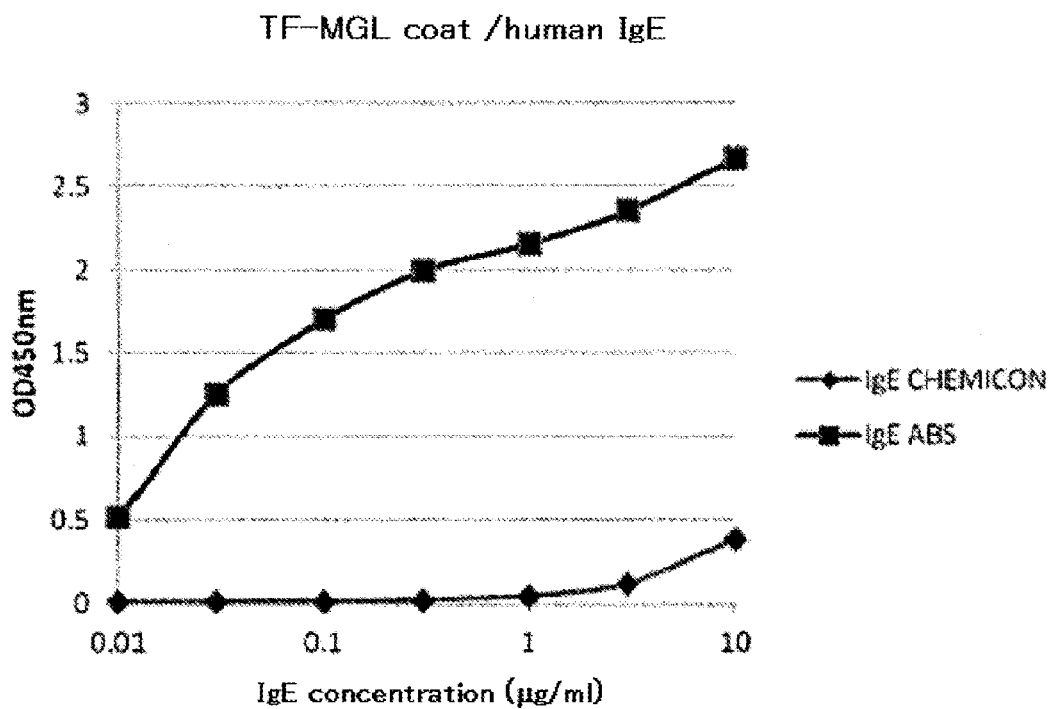
FIG. 8 shows the detection of a TF-MGL_1304 fusion protein by ELISA using the ABS IgE antibody and the CHEMICON human myeloma IgE antibody.

As a result, the ABS human monoclonal IgE antibody detected the TF-MGL_1304 fusion protein in a concentration dependent manner (FIG. 8). The result demonstrates that the ABS human monoclonal IgE antibody binds to the MGL_1304 protein and can detect the MGL_1304 protein quantitatively. On the other hand, the TF-MGL_1304 fusion protein was not sufficiently detected with the CHEMICON human myeloma IgE antibody (FIG. 8).

An ELISA plate was coated with the TF-MGL_1304 fusion protein (150 ng/well). The concentration of the ABS human monoclonal IgE antibody was varied in a wider range (0.02 to 20 ng/ml) and the immobilized recombinant MGL_1304 protein was detected by ELISA and a standard curve was created. The ABS IgE antibody binding to the TF-MGL_1304 fusion protein was detected with an HRP-labeled anti-human IgE antibody.

Figure 9:
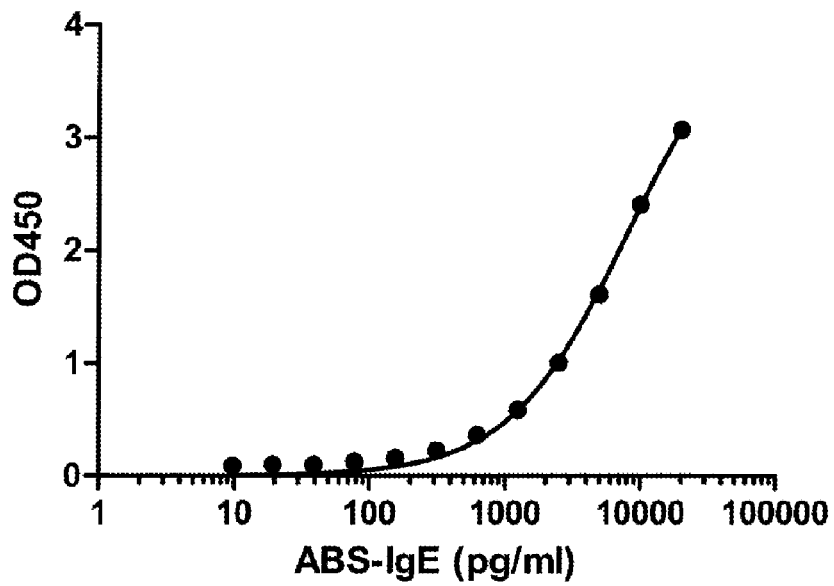
FIG. 9 shows the result of ELISA obtained using an immobilized recombinant MGL_1304 protein and the ABS IgE antibody at various concentrations, which demonstrates the concentration dependence of the detection of the recombinant MGL_1304 protein with the ABS IgE antibody.

As a result, the binding of the TF-MGL_1304 fusion protein and the ABS IgE antibody was quantitative (FIG. 9). The TF-MGL_1304 fusion protein is an antigen of sweat allergy (a sweat antigen) as described in Example 1-3. Therefore, those results demonstrate that the ABS IgE antibody can be used as a standard product at the time of quantification of IgE antibody that binds to a sweat antigen.

Example 7: Binding of ABS IgE Antibody to Other Antigens

An ELISA plate was coated with the partially purified sweat antigen (QRX) prepared in Example 1 (50 ng/well). ELISA plates were respectively coated with a mite antigen and a silk antigen expressed in *E. coli* (50 ng/well for each). It was studied by ELISA whether each antigen can be detected with the ABS IgE antibody. The ABS IgE antibody binding to each of the antigen was detected with an HRP-labeled anti-human IgE antibody.

Figure 10:
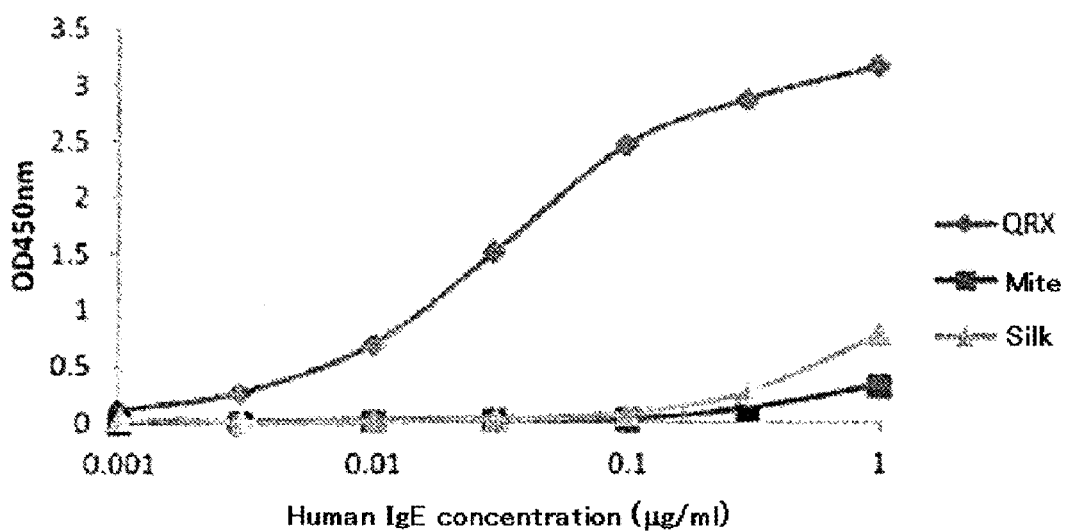
FIG. 10 shows that the ABS IgE antibody specifically binds to an immobilized QRX but not to immobilized mite and silk antigens.

As a result, the partially purified sweat antigen (QRX) was specifically detected with the ABS IgE antibody (FIG. 10).

Example 8: Comparison of QRX Detection Between ABS IgE Antibody and Smith2 Antibody An ELISA plate was coated with the partially purified sweat antigen (QRX) prepared in Example 1 (50 ng/well). The concentration was compared between the ABS IgE antibody and the Smith2 antibody (Accession No. FERM BP-11111) for detection of QRX. The ABS IgE antibody binding to QRX was detected with an HRP-labeled anti-human IgE antibody, and the Smith2 antibody bunding to QRX was detected with an HRP-labeled anti-mouse IgG antibody.

Figure 11:
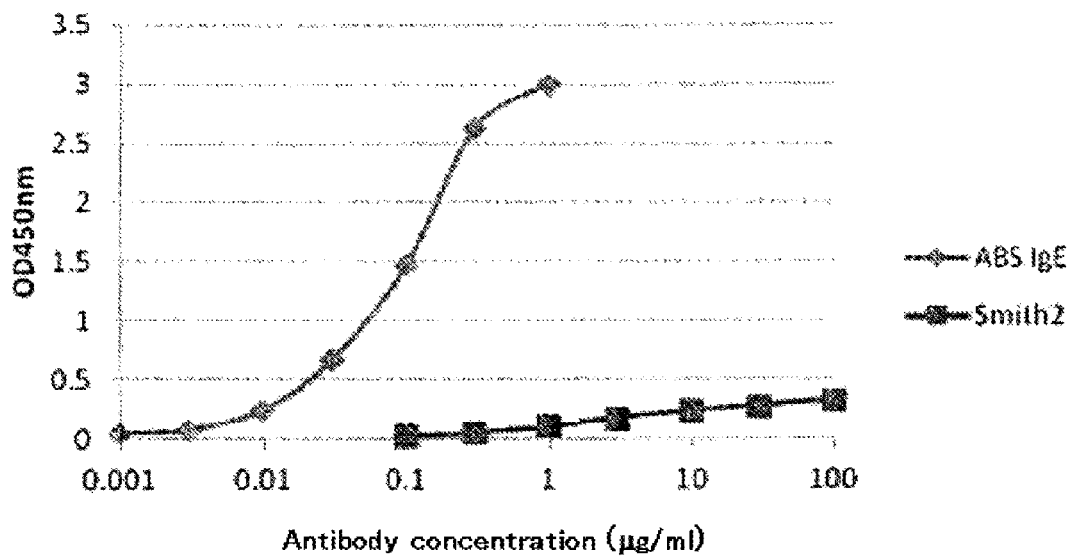
FIG. 11 shows that the concentration dependence of binding of the ABS IgE antibody or Smith2 antibody to QRX.

As a result, the ABS IgE antibody could detect the immobilized QRX from 0.01 μg/ml and the detection of QRX was saturated when the absorbance reached about three at 1 μg/ml, while the Smith2 antibody could detect QRX at 100 μg/ml with the absorbance of about 0.5. This result indicates that the ABS IgE antibody has an extremely high sensitivity to detect QRX compared to the Smith2 antibody (FIG. 11).

Example 9: ELISA Using ABS IgE Antibody and Smith2 Antibody

Since the results of Examples described above indicated that the ABS IgE antibody quantitatively bound to an antigen of sweat allergy (a sweat antigen), it was attempted to establish an ELISA system for detecting a sweat antigen at high sensitivity by using the ABS IgE antibody along with the Smith2 antibody binding to the sweat antigen.

Figure 12:
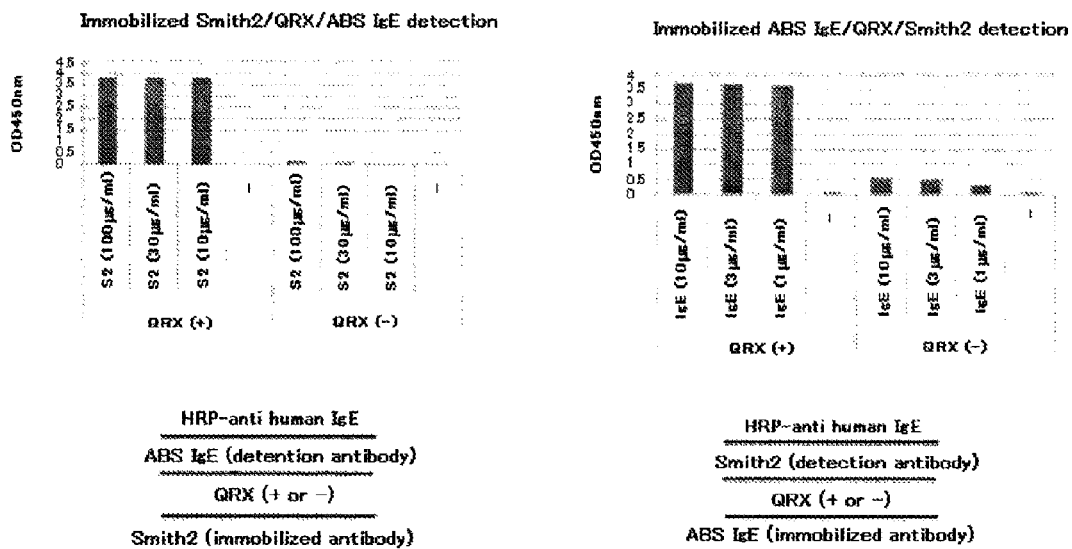
FIG. 12 shows the detection of QRX by sandwich ELISA using ABS IgE antibody and Smith2 antibody.

First, an ELISA system using the Smith2 antibody as an immobilized antibody and the ABS IgE antibody as a detection antibody was tested (this ELISA system is also referred to as ELISA system I hereinafter). Specifically, the Smith2 antibody was immobilized on an ELISA plate (10, 30, and 100 mg/ml, 50 μl/well) and, subsequently, QRX (1 mg/ml, 100 μl/well) or vehicle was added. Then the ABS IgE antibody (1 mg/ml, 100 μl/well) and an HRP-labeled anti-human IgE antibody (manufactured by KPL) were added and the absorbance (450 nm) was measured. As a result, while the absorbance without addition of QRX (background) was about zero, the absorbance was about 3.5 when QRX was added (FIG. 12).

Subsequently, an ELISA system using the ABS IgE antibody as an immobilized antibody and the Smith2 antibody as a detection antibody was tested (this ELISA system is referred to as ELISA system II hereinafter). Specifically, the ABS IgE antibody was immobilized on an ELISA plate (1, 3, and 10 µg/ml, 50 µl/well) and, subsequently, QRX (1 µg/ml, 100 µl/well) or vehicle was added. Then, the Smith2 antibody (10 µg/ml, 100 µl/well) and an HRP-labeled anti-mouse IgE antibody (manufactured by KPL) were added and the absorbance (450 nm) was measured. As a result, while the absorbance without addition of QRX (background) was about 0.5, the absorbance was about 3.5 when QRX was added (FIG. 12).

Figure 13:
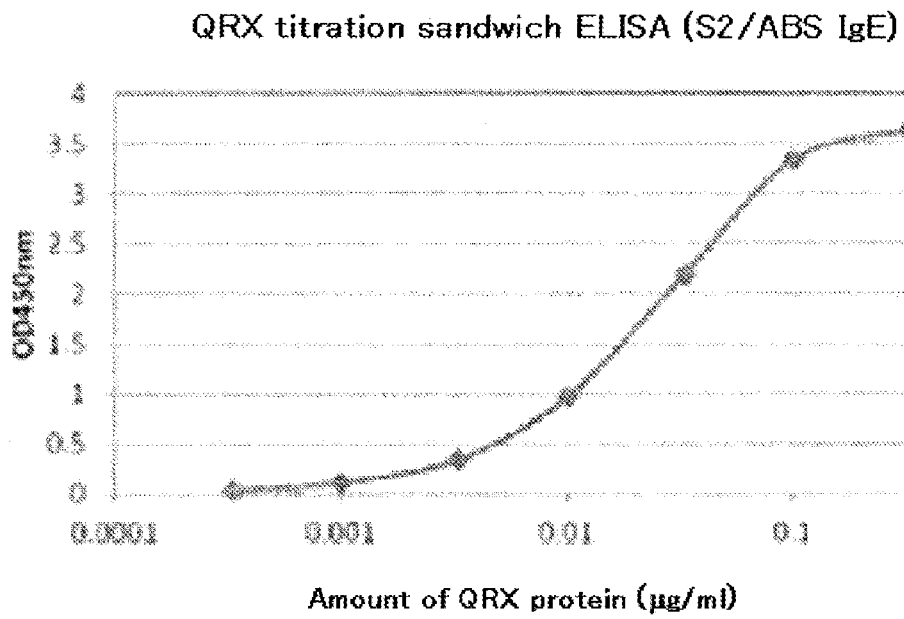
FIG. 13 shows a QRX titration curve in a system for detection of QRX by sandwich ELISA using the ABS IgE antibody and Smith2 antibody.

These results suggest that the former ELISA system (ELISA system I) using the Smith2 antibody as an immobilized antibody and the ABS IgE antibody as a detection antibody was superior to the latter ELISA system (ELISA system II). Therefore, it was studied whether the former ELISA system (ELISA system I) could detect QRX in a concentration-dependent manner. As a result, the ELISA system I detected QRX in a concentration-dependent manner (FIG. 13).

Figure 14:
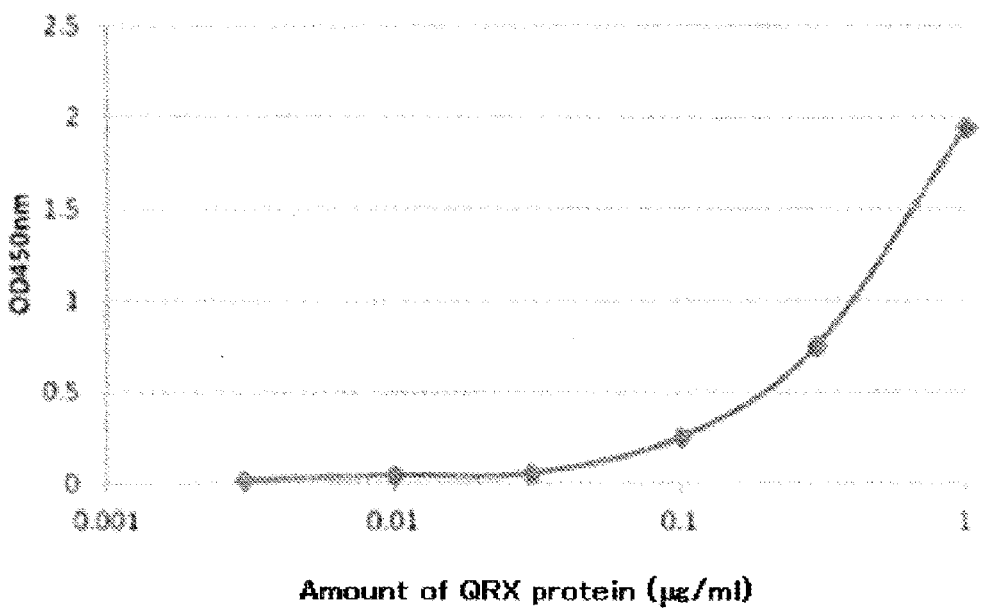
FIG. 14 shows a QRX titration curve from ELISA using the ABS IgE antibody for detection of QRX directly coated on a plate.

It was also demonstrated that the ELISA system I could detect QRX at about 300-times lower concentration as compared to an ELISA system in which QRX was directly immobilized on a plate and detected with the ABS IgE antibody (FIG. 14).

Then, it was studied whether the amount of the sweat antigen (QRX) contained in horny layer of human body surface could be measured by the ELISA system I. For collection of QRX in horny layer, a 2.5×2.5-cm square adhesive tape was affixed on body surface, peeled off, and dissolved in 500 µl 10-fold diluted RIPA buffer (Pierce: 25 mM Tris HCl pH 7.6, 150 mM NaCl, 1% NP-40, 1% sodium deoxycholate, 0.1% SDS) per tape.

Figure 15:
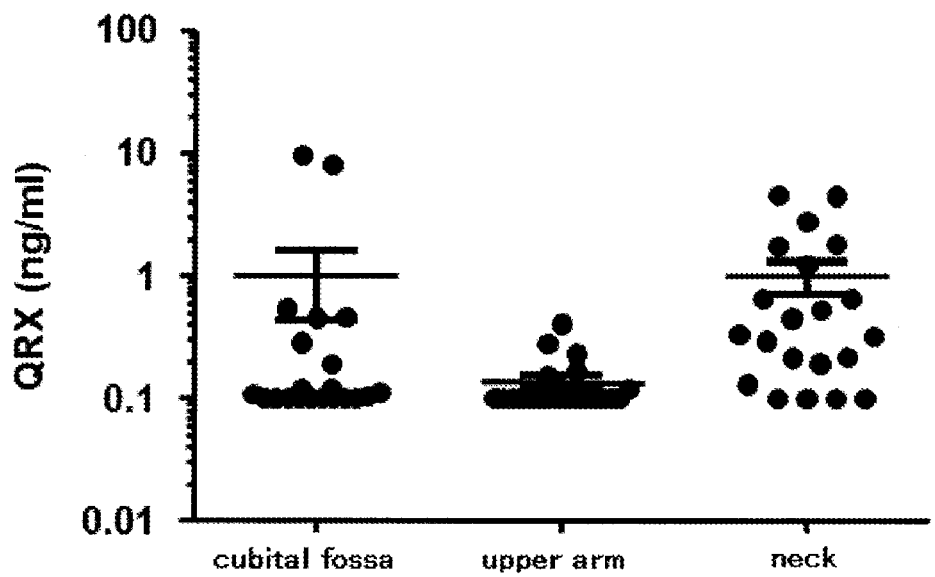
FIG. 15 shows the result of measurement of the amount of a sweat antigen (QRX) contained in horny layer of human body surface by sandwich ELISA using the ABS IgE antibody and Smith2 antibody.

As a result, it was revealed that QRX was contained in the cubital fossa at 1.01±2.64 ng/ml, in the upper arm at 0.13±0.078 ng/ml, in the neck at 1.01±1.38 ng/ml (FIG. 15).

Figure 16:
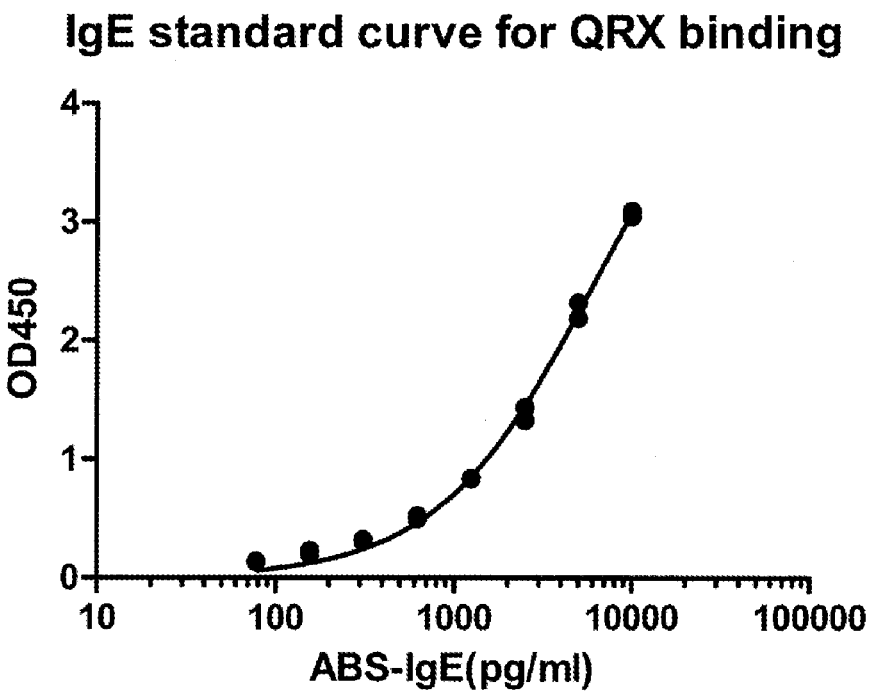
FIG. 16 shows the result of detection of QRX by sandwich ELISA using the ABS IgE antibody and Smith2 antibody with various concentrations of the ABS-IgE antibody.

Further, it was studied whether the amount of bound QRX varies when the concentration of the ABS IgE antibody was change. As a result, the absorbance varied depending on the concentration of the ABS IgE antibody (FIG. 16). Those results demonstrate that when the ABS IgE antibody is used as a standard substance in ELISA for a sample containing an IgE antibody that binds to QRX at an unknown concentration, the concentration of the antibody can be measured in an absolute concentration (e.g., pg/ml) of the ABS IgE antibody, not in absorbance.

Example 10: Western Blot Using ABS IgE Antibody

Figure 17:
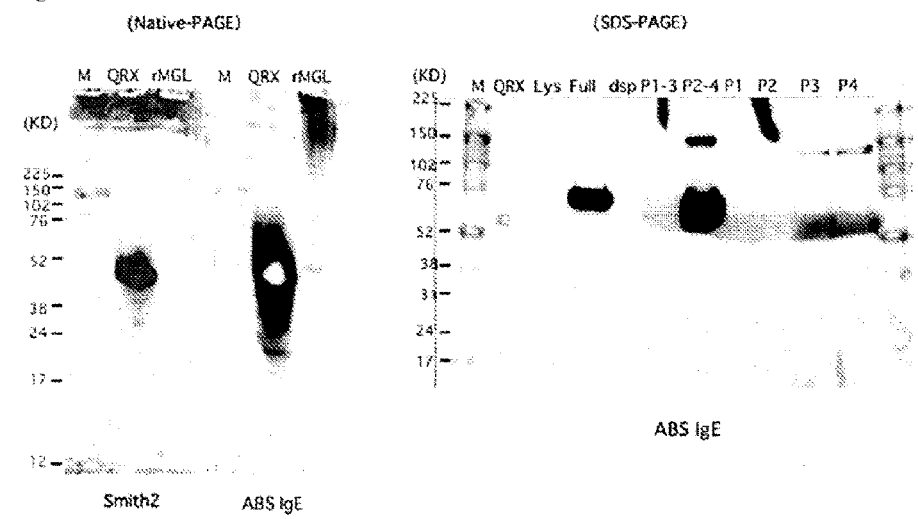
FIG. 17 shows the detection of QRX, a recombinant MGL_1304 protein, and a partial peptide of the recombinant MGL_1304 protein by Western blotting using the ABS IgE antibody.

By Western blotting, it was confirmed that the ABS IgE antibody recognized QRX and a recombinant MGL_1304 protein (obtained by removal of Trigger Factor (TF) from the TF-MGL_1304 fusion protein prepared in Example 3 by enzyme treatment), (FIG. 17).

The results of Western blotting using Native-PAGE and SDS-PAGE demonstrated that the ABS IgE antibody recognized both QRX and the MGL_1304 protein.

Further, it was studied whether the ABS IgE antibody recognized the following partial peptides of the MGL_1304 protein prepared by forced expression:

i) P1: a polypeptide corresponding to the amino acid sequence 1-50 (SEQ ID NO: 4) of the MGL_1304 protein;
ii) P2: a polypeptide corresponding to the amino acid sequence 46-100 (SEQ ID NO: 5) of the MGL_1304 protein;
iii) P3: a polypeptide corresponding to the amino acid sequence 96-140 (SEQ ID NO: 6) of the MGL_1304 protein;
iv) P4: a polypeptide corresponding to the amino acid sequence 136-183 (SEQ ID NO: 7) of the MGL_1304 protein;
v) P1-3: a polypeptide corresponding to the amino acid sequence 1-140 (SEQ ID NO: 8) of the MGL_1304 protein; and
vi) P2-4: a polypeptide corresponding to the amino acid sequence 46-183 (SEQ ID NO: 9) of the MGL_1304 protein.

As a result, the ABS IgE antibody bound mainly to the P3 and P4 regions (FIG. 17).

Example 11: Sweat Antigen Neutralizing Effect of ABS IgE Antibody

It was tested whether the ABS IgE antibody suppressed the histamine release induced by QRX from basophils derived from a sweat allergy patient.

As a result, the ABS IgE antibody suppressed the histamine release induced by QRX (FIG. 18).

It was also tested whether the ABS IgE antibody suppressed the histamine release activity of unpurified human sweat. Sweat was collected from patients, and the concentration of MGL1304 was adjusted to 1 µg/ml in each sweat sample. The sweat sample was added to basophils derived from a sweat allergy patient. Then, the results with and without the ABS IgE antibody (the final concentration of the ABS IgE antibody: 1 µg/ml) were compared.

As a result, the histamine release from basophils derived from an atopic dermatitis patient by QRX and unpurified sweat samples obtained from five patients was suppressed by the addition of the ABS IgE antibody (FIG. 19).

Example 12: Change in Reactivity to Sweat Antigen Due to Sensitization of Cell by ABS IgE Antibody To study whether mast cells or basophils respond to a sweat allergy antigen protein when the ABS IgE antibody binds to (sensitizes) a high-affinity IgE receptor expressed on the cells, a rat mast cell expressing a human high-affinity IgE receptor was sensitized by serum of an atopic dermatitis patient or the ABS IgE antibody and the histamine release by stimulation with QRX was examined.

As a result, when the cell was sensitized by serum of an atopic dermatitis patient, the degranulation was induced by stimulation with QRX (see "AD serum" in FIG. 20). However, the cell sensitized by the ABS IgE antibody did not show degranulation even when stimulated with QRX (see "ABS-IgE" in FIG. 20).

Further, basophils were prepared from blood samples of two human subjects and added with an anti-human IgE antibody (anti-IgE) that crosslinked IgE binding to an IgE receptor and activated the IgE receptor. As a result, the histamine release was observed from the basophils derived from both donors (see "untreated" in FIG. 21). When ORX, a partially purified sweat antigen, was added, weak histamine release was observed from the basophils derived from donor 1 and no histamine release was observed from the basophils derived from donor 2. When the mouse monoclonal antibody 6F7, which crosslinked an IgE receptor to which IgE did not bind and activate the IgE receptor, was added, moderate histamine release was observed from the basophils derived from both donors (see "untreated" of FIG. 21). Those results indicated that IgE bound to a part of IgE receptors in the basophils derived from both donors. Therefore, the basophils were treated with lactic acid such that IgE was dissociated from the IgE receptor and were stimulated in the same way. As a result, the level of the histamine release by the anti-IgE antibody decreased and the histamine release by QRX disappeared (see "lactic acid treatment" in FIG. 21). When these cells were further sensitized by the ABS IgE antibody and stimulated in the same way, the basophils derived from both donors reacted to the stimulation with the anti-human IgE antibody, while no histamine release was observed by QRX stimulation. The histamine release by the 6F7 stimulation disappeared or significantly decreased (see "IgE re-sensitization" in FIG. 21). The histamine release percentage due to the anti-IgE antibody did not become zero even when the basophils were treated with lactic acid because some of the high-affinity IgE receptors still had IgE bound thereto. Also, the histamine release percentage (net %) due to the anti-human IgE antibody stimulation was further reduced when the basophils of donor 2 were re-sensitized by IgE because the spontaneous histamine release percentage was increased by the treatment of the cells and the net release percentage was reduced. It was confirmed that IgE was dissociated from a large number of the high-affinity IgE receptors by the lactic acid treatment and the re-sensitization by IgE bound IgE again to a large number of the high-affinity IgE receptors, because the histamine release percentage due to the IgE-competitive anti-high-affinity-IgE receptor monoclonal antibody, 6F7, was increased by the lactic acid treatment and it was reduced or eliminated by the IgE re-sensitization.

These results indicate that the ABS IgE antibody binds to an IgE receptor on a cell but does not induce degranulation of mast cells even in the presence of an sweat allergy antigen.

Example 13: Measurement of Anti-Sweat Antigen-Specific IgE Antibody in Patient Serum (1)

It was studied whether an IgE antibody that specifically binds to a sweat antigen can be detected in serum of atopic dermatitis (AD) patients, allergic rhinitis patients, and healthy persons (Normal) by using the ELISA system prepared in Example 6 with an immobilized rTF-MGL (FIG. 9).

A 96-well ELISA plate was coated with rTF or rTF-MGL at 3 µg/ml and 50 µl/well and was left overnight at 4° C. The plate was washed twice, blocked by 2% BSA (room temperature, one hour), and then washed twice. The serum diluted 10 times (×10) or 20 times (×20) by 1% BSA was added at 100 µl/well and left for one hour at room temperature. After the plate was washed three times, a solution containing an HRP-labeled anti-human IgE antibody was added at 100 µl/well, left for one hour, and washed three times, and a color was developed with TMB for the measurement of absorbance (450 nm). The absorbance obtained from the well coated with rTF was subtracted from the absorbance obtained from the well coated with rTF-MGL and the amount of MGL-specific IgE binding was determined. The standard curve of the ABS IgE antibody described in Example 6 (FIG. 9) was created at the same time.

As a result, IgE that specifically bound to the sweat antigen (MGL) was detected in the serum of atopic dermatitis patients and allergic rhinitis patients by ELISA with immobilized rTF and rTF-rMGL and the concentration of the IgE antibody was quantified with the ABS IgE antibody as a standard substance (FIG. 22). On the other hand, in the serum of the healthy persons, IgE that bound to the sweat allergy antigen protein (rMGL) was at an extremely low value or equal to or less than the detection limit (100 pg/ml) (FIG. 22).

Those results indicate that sweat allergy can be diagnosed in atopic dermatitis and allergic rhinitis patients with the ABS IgE antibody as a standard substance.

Example 14: Measurement of Anti-Sweat Antigen-Specific IgE Antibody in Patient Serum (2)

The IgE antibody that specifically bound to a sweat antigen in serum of atopic dermatitis patients (AD1-3) and healthy persons (Normal1-2) was quantified with the ELISA system prepared in Example 9, in which a human IgE antibody was considered to bind to QRX bound to the immobilized Smith2 antibody (FIG. 16).

A 96-well ELISA plate was provided with the Smith2 antibody (10 µg/ml, 100 µl/well), left overnight at 4° C., washed twice, blocked by 2% BSA (room temperature, one hour), and washed twice. After QRX (1 µg/ml, 100 µl/well) was added, the plate was washed twice. The serum diluted 40 times (×40) or 80 times (×80) by 1% BSA was added at 100 µl/well and left for 90 minutes at room temperature. After the plate was washed three times, a solution containing an HRP-labeled anti-human IgE antibody was added at 100 µl/well, left for one hour, and washed three times, and a color was developed with TMB for the measurement of absorbance (450 nm). The standard curve (FIG. 16) was created at the same time by ELISA using the ABS IgE antibody as described in Example 9.

As a result, the concentration of IgE that was present in sweat and specifically bound to the sweat antigen which had been bound to the Smith2 antibody was quantified. The value roughly matched the value obtained in Example 13 regardless of the dilution rate of serum and the reproducibility of the quantification was observed (FIG. 23).

The invention claimed is:

1. A method of measuring an amount of a sweat allergy antibody in a sample from a human, comprising
   (a) contacting the sample comprising the sweat allergy antibody with a sweat allergy antigen protein having an amino acid sequence consisting of SEQ ID NO: 1 to form a complex and detecting the complex; and
   (b) determining the amount of the sweat allergy antibody in the sample based on a standard curve prepared by contacting a known concentration of a standard antibody with the sweat allergy antigen protein having an amino acid sequence consisting of SEQ ID NO: 1,
   wherein the standard antibody is a human IgE monoclonal antibody, clone HE1, that specifically binds to the sweat allergy antigen protein having an amino acid sequence consisting of SEQ ID NO: 1.

2. The method of claim 1, wherein the sweat allergy antibody is an IgE antibody.

3. The method of claim 1, wherein the amount of the sweat allergy antibody is measured in an ELISA plate on which the sweat allergy antigen protein is immobilized or an ELISA plate on which the sample is immobilized.

4. The method of claim 1, wherein said standard antibody does not induce degranulation in a reaction with the sweat allergy antigen protein having an amino acid sequence consisting of SEQ ID NO: 1.

* * * * *

SEQUENCE LISTING

<160> NUMBER OF SEQ ID NOS: 9

<210> SEQ ID NO 1
<211> LENGTH: 183
<212> TYPE: PRT
<213> ORGANISM: Malassezia globosa

<400> SEQUENCE: 1

Met Val Ser Leu Asn Ile Phe Ser Ala Ala Phe Val Ala Ser Leu Ala

```
               1               5                  10                 15
        Ser Ala Val Phe Ala Ala Pro Ser Ala Leu Glu Arg Arg Ala Ala Pro
                       20                  25                 30

Asp Asn Thr Val Trp Val Thr Ser Val Ala Asp His Cys Leu Ile Leu
                       35                  40                 45

Pro Arg His Lys Met Ser Val Gly Asp Ser Glu Ser Pro Gly Asn Met
                50                  55                 60

Arg Ser Phe Cys Thr Lys Pro Tyr Ser Ser Lys Gln Gly Gln Leu Ala
         65                  70                  75                 80

Ser Asp Phe Trp Thr Lys Ala His Phe Lys Lys Thr Asp Lys Tyr Val
                             85                  90                 95

Gln Ile Thr Gly Cys Ile Asn Pro Asn Val Gln Ser Thr Leu Leu Ser
                       100                 105                110

Asn Asp Glu Gly Gly Gln Tyr Asp Ser Asn Gly Glu Gly Gly Gly Arg
                       115                 120                125

Gly Asn Pro Ala Gly Ser Val Cys Leu Gly Tyr Ser Ser Tyr Val Glu
                       130                 135                140

Leu Val Glu Pro Ala Gly Asn Arg Ala Cys Ile Arg Cys Cys Tyr Asp
        145                 150                 155                160

Pro Ser Asp Cys Asp Val Ser Gln Asp Glu Ala Gly Cys Glu Thr Val
                            165                 170                175

Ile Pro Gly Lys Tyr Asp Cys
                       180

<210> SEQ ID NO 2
<211> LENGTH: 34
<212> TYPE: DNA
<213> ORGANISM: Artificial
<220> FEATURE:
<223> OTHER INFORMATION: PCR primer

<400> SEQUENCE: 2
ggggtaccgt atccctcaac attttctcag ctgc                                34

<210> SEQ ID NO 3
<211> LENGTH: 34
<212> TYPE: DNA
<213> ORGANISM: Artificial
<220> FEATURE:
<223> OTHER INFORMATION: PCR primer

<400> SEQUENCE: 3
cccaagcttt tagcagtcgt acttgccggg gatg                                34

<210> SEQ ID NO 4
<211> LENGTH: 50
<212> TYPE: PRT
<213> ORGANISM: Malassezia globosa

<400> SEQUENCE: 4

Met Val Ser Leu Asn Ile Phe Ser Ala Ala Phe Val Ala Ser Leu Ala
         1               5                  10                 15

Ser Ala Val Phe Ala Ala Pro Ser Ala Leu Glu Arg Arg Ala Ala Pro
                       20                  25                 30

Asp Asn Thr Val Trp Val Thr Ser Val Ala Asp His Cys Leu Ile Leu
                       35                  40                 45

Pro Arg
         50
```

<210> SEQ ID NO 5
<211> LENGTH: 55
<212> TYPE: PRT
<213> ORGANISM: Malassezia globosa

<400> SEQUENCE: 5

```
Leu Ile Leu Pro Arg His Lys Met Ser Val Gly Asp Ser Glu Ser Pro
1               5                   10                  15

Gly Asn Met Arg Ser Phe Cys Thr Lys Pro Tyr Ser Ser Lys Gln Gly
            20                  25                  30

Gln Leu Ala Ser Asp Phe Trp Thr Lys Ala His Phe Lys Lys Thr Asp
        35                  40                  45

Lys Tyr Val Gln Ile Thr Gly
    50                  55
```

<210> SEQ ID NO 6
<211> LENGTH: 45
<212> TYPE: PRT
<213> ORGANISM: Malassezia globosa

<400> SEQUENCE: 6

```
Val Gln Ile Thr Gly Cys Ile Asn Pro Asn Val Gln Ser Thr Leu Leu
1               5                   10                  15

Ser Asn Asp Glu Gly Gly Gln Tyr Asp Ser Asn Gly Gly Gly Gly Gly
            20                  25                  30

Arg Gly Asn Pro Ala Gly Ser Val Cys Leu Gly Tyr Ser
        35                  40                  45
```

<210> SEQ ID NO 7
<211> LENGTH: 43
<212> TYPE: PRT
<213> ORGANISM: Malassezia globosa

<400> SEQUENCE: 7

```
Ser Tyr Val Glu Leu Val Glu Pro Ala Gly Asn Arg Ala Cys Ile Arg
1               5                   10                  15

Cys Cys Tyr Asp Pro Ser Asp Cys Asp Val Ser Gln Asp Glu Ala Gly
            20                  25                  30

Cys Glu Thr Val Ile Pro Gly Lys Tyr Asp Cys
        35                  40
```

<210> SEQ ID NO 8
<211> LENGTH: 140
<212> TYPE: PRT
<213> ORGANISM: Malassezia globosa

<400> SEQUENCE: 8

```
Met Val Ser Leu Asn Ile Phe Ser Ala Ala Phe Val Ala Ser Leu Ala
1               5                   10                  15

Ser Ala Val Phe Ala Ala Pro Ser Ala Leu Glu Arg Arg Ala Ala Pro
            20                  25                  30

Asp Asn Thr Val Trp Val Thr Ser Val Ala Asp His Cys Leu Ile Leu
        35                  40                  45

Pro Arg His Lys Met Ser Val Gly Asp Ser Glu Ser Pro Gly Asn Met
    50                  55                  60

Arg Ser Phe Cys Thr Lys Pro Tyr Ser Ser Lys Gln Gly Gln Leu Ala
65                  70                  75                  80

Ser Asp Phe Trp Thr Lys Ala His Phe Lys Lys Thr Asp Lys Tyr Val
                85                  90                  95
```

```
Gln Ile Thr Gly Cys Ile Asn Pro Asn Val Gln Ser Thr Leu Leu Ser
            100                 105                 110

Asn Asp Glu Gly Gly Gln Tyr Asp Ser Asn Gly Gly Glu Gly Gly Arg
        115                 120                 125

Gly Asn Pro Ala Gly Ser Val Cys Leu Gly Tyr Ser
    130                 135                 140

<210> SEQ ID NO 9
<211> LENGTH: 138
<212> TYPE: PRT
<213> ORGANISM: Malassezia globosa

<400> SEQUENCE: 9

Leu Ile Leu Pro Arg His Lys Met Ser Val Gly Asp Ser Glu Ser Pro
1               5                   10                  15

Gly Asn Met Arg Ser Phe Cys Thr Lys Pro Tyr Ser Ser Lys Gln Gly
            20                  25                  30

Gln Leu Ala Ser Asp Phe Trp Thr Lys Ala His Phe Lys Lys Thr Asp
        35                  40                  45

Lys Tyr Val Gln Ile Thr Gly Cys Ile Asn Pro Asn Val Gln Ser Thr
    50                  55                  60

Leu Leu Ser Asn Asp Glu Gly Gly Gln Tyr Asp Ser Asn Gly Gly Glu
65                  70                  75                  80

Gly Gly Arg Gly Asn Pro Ala Gly Ser Val Cys Leu Gly Tyr Ser Ser
            85                  90                  95

Tyr Val Glu Leu Val Glu Pro Ala Gly Asn Arg Ala Cys Ile Arg Cys
            100                 105                 110

Cys Tyr Asp Pro Ser Asp Cys Asp Val Ser Gln Asp Glu Ala Gly Cys
        115                 120                 125

Glu Thr Val Ile Pro Gly Lys Tyr Asp Cys
    130                 135
```